United States Patent
Biggadike et al.

(10) Patent No.: US 6,197,761 B1
(45) Date of Patent: Mar. 6, 2001

(54) 17β-2-OXO-TETRAHYDROFURANYL)-CARBOTHIOIC ACID ESTER, -CARBOXYLIC ACID ESTER AND -CARBOXYLIC ACID AMIDE ANDROSTANE DERIVATIVES

(75) Inventors: Keith Biggadike; Panayiotis Alexandrou Procopiou, both of Stevenage (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/091,748

(22) PCT Filed: Dec. 19, 1996

(86) PCT No.: PCT/GB96/03140

§ 371 Date: Jun. 24, 1998

§ 102(e) Date: Jun. 24, 1998

(87) PCT Pub. No.: WO97/24365

PCT Pub. Date: Jul. 10, 1997

(30) Foreign Application Priority Data

Dec. 29, 1995 (GB) .................................. 9526651
Jun. 21, 1996 (GB) .................................. 9613121

(51) Int. Cl.$^7$ .................... A61K 31/58; A61K 31/56; C07J 71/00; C07D 307/02; A61P 37/08
(52) U.S. Cl. ..................... 514/174; 514/181; 540/67; 540/70; 540/71; 549/475
(58) Field of Search ................. 514/174, 181; 540/67, 70, 71; 549/475

(56) References Cited

U.S. PATENT DOCUMENTS 4,093,721   6/1978   Phillips et al. ............... 424/243
5,767,113  * 6/1998   Cohn et al. .................. 514/180

FOREIGN PATENT DOCUMENTS 0 143 764   6/1985   (EP).
0 200 692  11/1986   (EP).
2 018 256  10/1979   (GB).

OTHER PUBLICATIONS

Journal De Pharmacie De Beligique, vol. 46, No. 1, 1991, pp. 37–48, P.A. Formstecher et al.
Journal of Medicinal Chemistry, vol. 37, No. 22, Oct. 1994, Washington, US, pp. 3717–3729, G.H. Phillips et al, "Synthesis and Structure–Activity Relationships in a Series of Antiinflammatory Corticosteroid Analogues, Halomethyl Androstane–17.beta.–carbothioates and 17.beta.–Carboselenoates".

* cited by examiner

Primary Examiner—Mukund J. Shah
Assistant Examiner—Brenda Coleman
(74) Attorney, Agent, or Firm—Nixon & Vanderhye

(57) ABSTRACT

Compounds of the androstane series are described having general formula

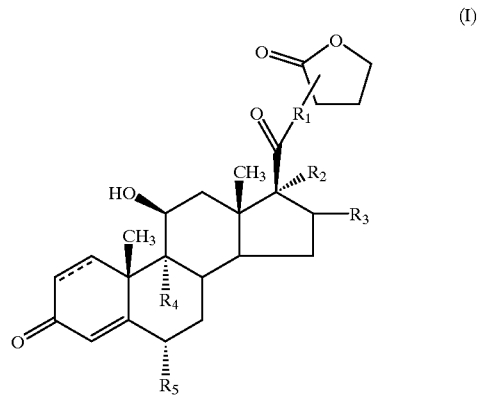

(I)

and solvates thereof, in which $R_1$ represents O, S or NH; $R_2$ individually represents OC(=O)$C_{1-6}$ alkyl; $R_3$ individually represents hydrogen, methyl (which may be in either the α or β configuration) or methylene; or $R_2$ and $R_3$ together represent

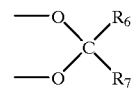

where $R_6$ and $R_7$ are the same or different and each represents hydrogen or $C_{1-6}$ alkyl; $R_4$ and $R_5$ are the same or different and each represents hydrogen or halogen and === represents a single or a double bond. These compounds and their solvates have use in medicine as antiinflammatory or anti-allergic agents.

27 Claims, No Drawings

17β-2-OXO-TETRAHYDROFURANYL)-CARBOTHIOIC ACID ESTER, -CARBOXYLIC ACID ESTER AND -CARBOXYLIC ACID AMIDE ANDROSTANE DERIVATIVES

This application is a national stage entry under 35 U.S.C. §371 of PCT/GB96/03140, filed Dec. 19, 1996.

The present invention relates to novel anti-inflammatory and anti-allergic compounds of the androstane series and to processes for their preparation. The present invention also relates to pharmaceutical formulations containing the compounds and to therapeutic uses thereof, particularly for the treatment of inflammatory and allergic conditions.

Glucocorticosteroids which have anti-inflammatory properties are known and are widely used for the treatment of inflammatory disorders or diseases such as asthma and rhinitis. However, glucocorticosteroids in general may suffer from the disadvantage of causing unwanted systemic effects following administration. WO94113690, WO94/14834, WO92/13873 and WO92/13872 all disclose glucocorticosteroids which are alleged to possess anti-inflammatory activity coupled with reduced systemic potency.

The present invention provides a novel group of compounds which possess useful anti-inflammatory activity whilst having little or no systemic activity. Thus, the compounds of the present invention represent a safer alternative to those known glucocorticoids which have poor side-effect profiles.

Thus, according to one aspect of the invention, there is provided a compound of formula (I)

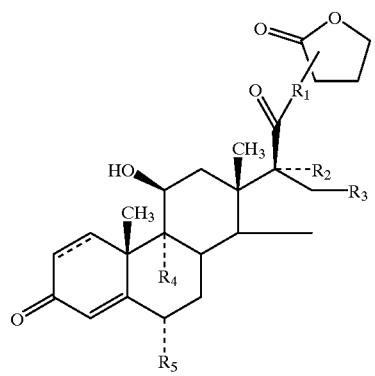

(I)

and solvates thereof, in which $R_1$ represents O, S or NH;
$R_2$ individually represents $OC(=O)C_{1-6}$ alkyl;
$R_3$ individually represents hydrogen, methyl (which may be in either the α or β configuration) or $=CH_2$;
or $R_2$ and $R_3$ together represent

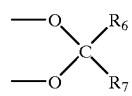

wherein $R_6$ and $R_7$ are the same or different and each represents hydrogen or $C_{1-6}$ alkyl;
$R_4$ and $R_5$ are the same or different and each represents hydrogen or halogen; and ≡≡≡ represents a single or a double bond.

In the above definitions, the term "alkyl" as a group or part of a group means a straight chain, or, where available, a branched chain alkyl moiety. For example, it may represent a $C_{1-4}$ alkyl function as represented by methyl, ethyl, n-propyl, i-propyl, n-butyl and t-butyl.

The solvates may, for example, be hydrates.

References hereinafter to a compound according to the invention includes both compounds of formula (I) and solvates thereof, particularly pharmaceutically acceptable solvates.

It will be appreciated that the invention includes within its scope all stereoisomers of the compounds of formula (I) and mixtures thereof.

In particular the compounds of formula (I) contain an asymmetric centre at the point of attachment of the lactone moiety. Thus, the invention includes within its scope both diastereoisomers at this asymmetric centre and mixtures thereof.

Diastereoisomers and mixtures thereof at the asymmetric centre formed when $R_2$ and $R_3$ together represent

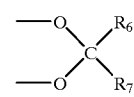

and $R_6$ and $R_7$ are different are also included within the scope of the present invention.

$R_1$ can be bonded to the alpha, beta or gamma carbon atoms of the lactone group,

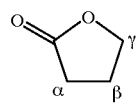

however, compounds of formula (I) in which $R_1$ is bonded to the alpha atom are generally preferred.

A preferred group of compounds of the invention are compounds of formula (I) in which $R_1$ represents O or S, especially S.

A further preferred group of compounds of the invention are compounds of formula (I) in which $R_2$ individually represents $OC(=O)C_{1-6}$ alkyl, more preferably $OC(=O)C_{1-3}$ alkyl, especially $OC(=O)$ethyl. Compounds within this group in which $R_3$ is methyl are generally preferred.

Another preferred group of compounds are compounds of formula (I) in which $R_2$ and $R_3$ together represent

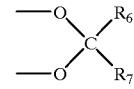

wherein $R_6$ and $R_7$ are the same or different and each represents hydrogen or $C_{1-6}$ alkyl, particularly hydrogen or $C_{1-3}$ alkyl, especially hydrogen, methyl or n-propyl.

Compounds of formula (I) in which $R_4$ and $R_5$, which can be the same or different, each represents hydrogen, fluorine or chlorine, particularly hydrogen or fluorine, are preferred. Especially preferred are compounds in which both $R_4$ and $R_5$ are fluorine.

A particularly preferred group of compounds of the present invention are compounds of formula (I) in which $R_1$ is S; $R_2$ is $OC(=O)C_{1-6}$ alkyl, particularly $OC(=O)C_{1-3}$ alkyl, especially $OC(=O)$ethyl; $R_3$ is methyl; $R_4$ and $R_5$, which can be the same or different, each represents hydrogen or fluorine, especially fluorine, and ≡≡≡ represents a single or a double bond.

A further particularly preferred group of compounds of the invention are compounds of formula (I) in which $R_1$ is S; $R_2$ and $R_3$ together represent

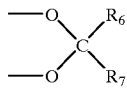

wherein $R_6$ and $R_7$ are the same or different and each represents hydrogen or $C_{1-6}$ alkyl, particularly hydrogen or $C_{1-3}$ alkyl, especially hydrogen, methyl or n-propyl; $R_4$ and $R_5$ which can be the same or different each represents hydrogen or fluorine, especially fluorine; and ═ represents a single or a double bond. The R-isomers of compounds within this group in which $R_6$ and $R_7$ are different are preferred.

It is to be understood that the present invention covers all combinations of particularly and preferred groups referred to hereinabove.

Compounds of formula (I) include:
17α-Butyryloxy-6α,9α-difluoro-11β-hydroxy-16α-methyl-3-oxo-androsta-1,4-diene-17β-carbothioic acid S-(2-oxo-tetrahydro-furan-3-yl) ester;
17α-Acetyloxy-6α,9β-difluoro-11β-hydroxy-16α-methyl-3-oxo-androsta-1,4-diene-17β-carbothioic acid S-(2-oxo-tetrahydro-furan-3-yl) ester;
9α-Fluoro-11β-hydroxy-16β-methyl-3-oxo-17α-propionyloxy-androsta-1,4-diene-17β-carbothioic acid S-(2-oxo-tetrahydro-furan-3-yl) ester;
6α,9β-Difluoro-11β-droxy-16α-methyl-3-oxo-17α-propionyloxy-androsta-1,4-diene-17β-carbothioic acid S-(5-oxo-tetrahydro-furan-2-yl) ester;
6α,9α-Difluoro-11β-hydroxy-16α-methyl-3-oxo-17α-propionyloxy-androsta-1,4-diene-17β-carbothioic acid S-(2-oxo-tetrahydro-furan-4-yl) ester;
6α,9α-Difluoro-11β-hydroxy-16α-methyl-3-oxo-17α-propionyloxy-androsta-1,4-diene-17β-carboxylic acid (2-oxo-tetrahydro-furan-3-yl) ester;
6α,9α-Difluoro-11β-hydroxy-16α-methyl-3-oxo-17α-propionyloxy-androsta-1,4-diene-17β-carboxylic acid (2-oxo-tetrahydro-furan-5-yl) ester;
6α,9α-Difluoro-11β-hydroxy-16α,17α-isopropylidenedioxy-3-oxo-androsta-1,4-diene-17β-carbothioic acid S-(2-oxo-tetrahydro-furan-5-yl) ester;
6α,9α-Difluoro-11β-hydroxy-16α,17α-isopropylidenedioxy-3-oxo-androst-4-ene-17β-carbothioic acid S-(2-oxo-tetrahydro-furan-3-yl) ester;
6α,9α-Difluoro-11β-hydroxy-16α,17α-isopropylidenedioxy-3-oxo-androsta-1,4-diene-17β-carboxylic acid N-(2-oxo-tetrahydro-furan-3-yl) amide;
6α,9α-Difluoro-11β-hydroxy-16α,17α-isopropylidenedioxy-3-oxo-androsta-1,4-diene-17β-carboxylic acid (2-oxo-tetrahydro-furan-3-yl) ester;
16α,17α-Butylidenedioxy-11β-hydroxy-3-oxo-androsta-1,4-diene-17β-carbothioic acid S-(2-oxo-tetrahydro-furan-3-yl) ester;
16α,17α-(R-Butylidenedioxy)-6α,9α-difluoro-11β-hydroxy-3-oxo-androsta-1,4-diene-17β-carbothioic acid S-(2-oxo-tetrahydro-furan-3-yl) ester,
16α,17α-Butylidenedioxy-11β-hydroxy-3-oxo-androsta-1,4-diene-17β-carboxylic acid (2-oxo-tetrahydro-furan-3-yl) ester;
16α,17α-(R-Butylidenedioxy)-6α,9α-difluoro-11β-hydroxy-3-oxo-androst-4-ene-17β-carboxylic acid N-(2-oxo-tetrahydro-furan-3-yl) amide;
6α,9α-Difluoro-11β-hydroxy-16α,17α-isopropylidenedioxy-3-oxo-androsta-1,4-diene-17β-carboxylic acid N-(2-oxo-tetrahydro-furan-4-yl) amide;
16α,17α-(R-Butylidenedioxy)-6α,9α-difluoro-11β-hydroxy-3-oxo-androst-4-ene-17β-carbothioic acid (5-oxo-tetrahydro-furan-2-yl) ester; and solvates thereof.

Preferred compounds of formula (I) include:
6α,9α-Difluoro-11β-hydroxy-16α-methyl-3-oxo-17α-propionyloxy-androsta-1,4-diene-17β-carbothioic acid S-(2-oxo-tetrahydro-furan-3-yl) ester;
6α,9α-Difluoro-11β-hydroxy-16α-methyl-3-oxo-17α-propionyloxy-androst4-ene-17β-carbothioic acid S-(2-oxo-tetrahydro-furan-3-yl) ester;
6α,9α-Difluoro-11β-hydroxy-16α,17α-isopropylidenedioxy-3-oxo-androsta-1,4-diene-17β-carbothioic acid S-(2-oxo-tetrahydro-furan-3-yl) ester;
16α,17α-(R-Butylidenedioxy)-6α,9α-difluoro-11β-hydroxy-3-oxo-androst-4-ene-17β-carbothioic acid S-(2-oxo-tetrahydro-furan-3-yl) ester;
and solvates thereof.

It will be appreciated that each of the above compounds of formula (I) includes the individual R and S diastereoisomers at the asymmetric centre at the point of attachment of the lactone moiety as well as the mixtures thereof. It will further be appreciated that the compounds of formula (I) may include the individual R and S diastereoisomers at the asymmetric centre formed when $R_2$ and $R_3$ together represent

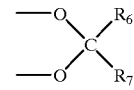

wherein $R_6$ and $R_7$ are different, as well as mixtures thereof.

Thus, the individual R and S diastereoisomers isolated such as to be substantially free of the other diastereoisomer ie pure and mixtures thereof are included within the scope of the present invention. An individual R or S diastereoisomer isolated such as to be substantially free of the other diastereoisomer ie pure will preferably be isolated such that less than 10% preferably less than 1% especially less than 0.1% of the other diastereoisomer is present.

The compounds of formula (I) have potentially beneficial anti-inflammatory or anti-allergic effects, particularly upon topical administration, demonstrated by, for example, their ability to bind to the glucocorticoid receptor and to illicit a response via that receptor. Hence, the compounds of formula (I) are useful in the treatment of inflammatory and/or allergic disorders. Further, compounds of formula (I) possess the advantage of having little or no systemic activity. Therefore, the compounds of the invention may represent a safer alternative to those known anti-inflammatory glucocorticoids which have poor side effect profiles.

Examples of disease states in which the compounds of the invention have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory and anti-allergic agents.

There is thus provided as a further aspect of the invention a compound of formula (I) or a physiologically acceptable solvate thereof for use in human or veterinary medicine, particularly in the treatment of patients with inflammatory and/or allergic conditions.

According to another aspect of the invention, there is provided the use of a compound of formula (I) or physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof.

The compounds according to the invention may be formulated for administration in any convenient way, and the invention therefore also includes within its scope pharmaceutical compositions comprising a compound of formula (I) or physiologically acceptable solvate thereof together, if desirable, in admixture with one or more physiologically acceptable diluents or carriers.

Further, there is provided a process for the preparation of such pharmaceutical compositions which comprises mixing the ingredients.

The compounds according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

Advantageously, the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 $\mu$g–10 mg of the compound of formula (I). Alternatively, the compound of the invention may be presented without excipients such as lactose.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will be within the range of from 0.1 to 5%.

Aerosol formulations are preferably arranged so that each metered dose or "puff" of aerosol contains 20 $\mu$g–2000 $\mu$g, preferably about 20 $\mu$g–500 $\mu$g of a compound of formula (I). Administration may be once daily or several times daily, for example 2, 3, 4 or 8 times, giving for example 1, 2 or 3 doses each time. The overall daily dose with an aerosol will be within the range 100 $\mu$g–10 mg preferably, 200 $\mu$g–2000 $\mu$g. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5–30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising a compound of formula (I) or a physiologically acceptable solvate thereof together with another therapeutically active agent, for example, a $\beta_2$-adrenoreceptor agonist, an anti-histamine or an anti-allergic.

The combination referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The compounds of formula (I) and solvates thereof may be prepared by the methodology described hereinafter, constituting a further aspect of this invention.

Thus, according to a first process (A), a compound of formula (I) may be prepared by treating a compound of formula (II)

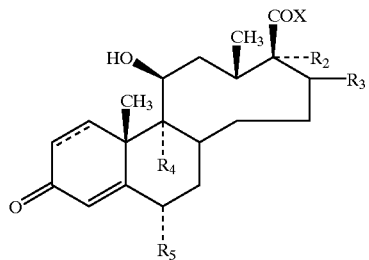

(II)

in which $R_2$, $R_3$, $R_4$, $R_5$ and ═══ are as defined hereinbefore for compounds of formula (I) and X represents OH or an activated derivative thereof such as a triazole or a mixed anhydride, with a compound of formula (III)

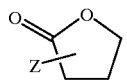

(III)

and salts thereof, in which

Z represents OH, $NH_2$ or SH.

Thus, a compound of formula (II) wherein X represents OH may be activated with an activating agent such as a triazole e.g. 1-hydroxy-benzotriazole and a carbodiimide such as 1-(3-dimethylamino-propyl)-3-ethyl-carbodiimide hydrochloride in a polar solvent such as dimethylformamide, conveniently at elevated temperatures e.g. about 100° C., and under an inert atmosphere such as nitrogen or the like, to form an activated derivative of the compound of formula (II), such as a triazole derivative e.g. a benzotriazole derivative of formula (IV)

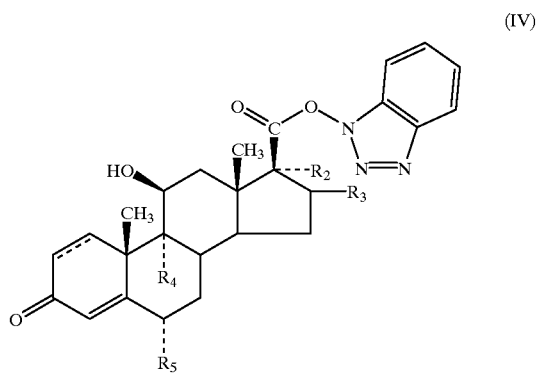

(IV)

(in which $R_2$, $R_3$, $R_4$, $R_5$ and ═══ are as defined hereinbefore).

The activated derivative, which may be isolated if required, is reacted with a compound of formula (III) wherein Z represents $NH_2$, SH or OH to form the desired compound of formula (I).

It will be appreciated by those skilled in the art that the coupling reaction may take place in one step without the isolation of the activated derivative if a compound of formula (III) is present during or added following activation. Alternatively, the activated derivative may be isolated and then subsequently treated with a compound of formula (III) to form the desired compound of formula (I).

Both methods are included within the scope of the present invention.

Compounds of formula (I) may also be prepared according to the above process (A) by coupling a compound of formula (II) wherein X represents OH with a compound of formula (III) wherein Z represents SH, OH or $NH_2$ via an intermediate mixed anhydride, for example, a mixed phosphate anhydride such as a compound of formula (V) as described by Kertesz and Marx in the Journal of Organic Chemistry, 1986, 51, 2315–2328.

Thus, a compound of formula (II) wherein X represents OH may be activated with an activating agent, such as diethylchlorophosphate in the presence of a base such as a tertiary amine e.g. triethylamine and in a suitable solvent such as a chlorinated solvent e.g. dichloromethane to form an activated derivative of the compound of formula (II) e.g. a diethylphosphate mixed anhydride derivative of formula (V)

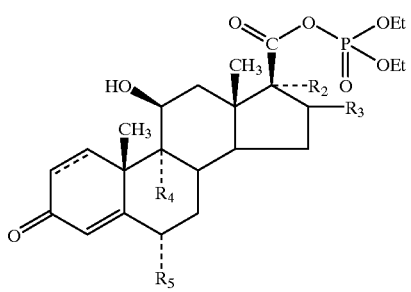

(V)

(in which $R_2$, $R_3$, $R_4$, $R_5$ and ═══ are as defined hereinbefore).

The activated derivative, which may be isolated if required, is reacted with a compound of formula (III) wherein Z represents SH, OH or $NH_2$ to form the desired compound of formula (I).

It will be appreciated by those skilled in art that the coupling reaction may take place without the isolation of the activated derivative if a compound of formula (III) is present during or added following activation. Alternatively, the activated derivative may be isolated and then subsequently treated with a compound of formula (III) to form the desired compound of formula (I).

Both methods are included within the scope of the present invention.

Compounds of formula (I) wherein $R_1$ represents O or S may also be prepared according to a second process (B) in which a compound of formula (II) in which $R_2$, $R_3$, $R_4$, $R_5$ and ═══ are as defined hereinbefore and X represents OH or SH or their corresponding salts, is treated with a compound of formula (VI) or formula (VII)

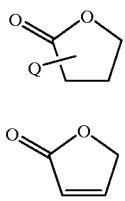

(VI)

(VII)

in which Q represents a suitable leaving group (such as Cl, Br, $OSO_2A$ wherein A is, for example $CH_3$, $CF_3$, p-$CH_3C_6H_4$), under standard methods.

The above general process (B) employing compounds of formula (VI) can be used to prepare compounds of formula (I) in which $R_1$ is linked to the alpha, beta, or gamma carbon atoms of the lactone group.

Compounds of formula (I) wherein $R_1$ represents O or S may be prepared according to the above process (B) by alkylation of a compound of formula (II) wherein X represents OH or SH respectively, with a compound of formula (VI) wherein Q represents a suitable leaving group using methods known in the art, or an adaptation of those methods.

Thus, for example, a compound of formula (I) wherein $R_1$ represents O may be prepared by alkylation of a compound of formula (II) wherein X represents OH conveniently in the form of an appropriate salt (such as alkali metal e.g. sodium or quarternaryammonium salt) with a compound of formula (VI) wherein Q represents a suitable leaving group, preferably chlorine, bromine or mesylate. The alkylation reaction is preferably carried out in the presence of a solvent, suitably a polar solvent, under inert conditions, for example, nitrogen or the like, conveniently at a temperature of between about 0° C. to 100° C. Suitable polar solvents may include acetone, dimethylformamide, dimethyl acetamide, dimethylsulphoxide, dichloromethane or chloroform.

Similarly, compounds of formula (I) wherein $R_1$ represents S can be prepared according to the above process (B) by alkylation of a compound of formula (II) wherein X represents SH with a compound of formula (VI) wherein Q represents a suitable leaving group by adaptation of the methods described by Phillipps et al, Journal of Medicinal Chemistry, 1994, 37, 3717–3729. Thus, a compound of formula (I) wherein $R_1$ represents S may be prepared by alkylation of the corresponding compound of formula (II) wherein X represents SH conveniently in the form of an appropriate salt (such as alkali metal e.g. sodium or quarternaryammonium salt) with a compound of formula (VI) wherein Z represents a suitable leaving group as described hereinabove for similar alkylation reactions.

Alternatively, compounds of formula (I) wherein $R_1$ represents O or S may be prepared according to the above process (B) by alkylation of a compound of formula (II) wherein X represents OH or SH with a compound of formula (VI) wherein Q represents OH under Mitsunobu conditions using triphenylphosphine and a dialkyl azodicarboxylate, or by using Vilsmeier methodology as described by Barrett and Procopiou in the Journal of the Chemical Society, Chemical Communications, 1995, 1403–1404.

A compound of formula (I) wherein $R_1$ represents S and is bonded to the beta carbon atom of the lactone group may also be prepared by reacting the corresponding compound of formula (II) wherein X represents SH with a compound of formula (VII). For example, by Michael addition of the compound of formula (II) with the compound of formula (VII) in the presence of a base such as potassium carbonate and in a suitable solvent such as dimethylforamide.

Compounds of formula (I) may also be prepared from other compounds of formula (I) thereof using conventional interconversion procedures such as transacetalisation, epimerisation or esterification. Thus, a process for preparing a compound of formula (I) by interconversion of another compound of formula (I) (process C) constitutes a further aspect of the present invention.

Compounds of formula (I) having a 1,2 single bond may be prepared by partial reduction of the corresponding 1,2 double bond compound by conventional methods. Thus, for example, by hydrogenation of the corresponding compound of formula (I) or of an intermediate used for the preparation of a compound of formula (I) using a palladium catalyst, conveniently in a suitable solvent e.g. ethyl acetate or preferably by using tris(triphenylphosphine) rhodium (I) chloride (known as Wilkinson's catalyst), conveniently in a suitable solvent such as toluene, ethyl acetate or ethanol.

It will be appreciated by those skilled in the art that it may be desirable to use protected derivatives of intermediates used in the preparation of compounds of formula (I). Thus, the above processes may require deprotection as an intermediate or final step to yield the desired compound. Thus, according to another process (D), a compound of formula (I) may be prepared by subjecting a protected derivative of a compound of formula (I) to reaction to remove the protecting group or groups present, constituting a further aspect of the present invention.

Protection and deprotection of functional groups may be effected using conventional means. Thus, hydroxyl groups may be protected using any conventional hydroxyl protecting group, for example, as described in Protective Groups in Organic Chemistry, Ed. J. F. W. McOmie (Plenum Press, 1973) or Protective Groups in Organic Synthesis by Theodora W. Green (John Wiley and Sons, 1991).

Examples of suitable hydroxyl protecting groups includes groups selected from alkyl (e.g. t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyidimethylsilyl). The hydroxyl protecting groups may be removed by conventional techniques. Thus, for example alkyl, silyl, acyl and heterocyclic groups may be removed by solvolysis, e.g. by hydrolysis under-acidic or basic conditions. Aralkyl groups such as triphenylmethyl may be similarly be removed by solvolysis, e.g. by hydrolysis under acidic conditions. Aralkyl groups such as benzyl may be cleaved by hydrogenolysis in the presence of a Noble metal catalyst such as palladium-on-charcoal.

The compounds of formulae (II), (III), (IV), (V), (VI) and (VII) are either generally known compounds or may be prepared by methods analogous to those described in the art for preparing the known compounds of formula (II), (III), (IV), (V), (VI) and (III) or may be prepared by the methods described herein. Novel compounds of formulas (II), (III), (IV), (V) and (VI) form yet a further aspect of the present invention.

For example, the compounds of formula (II) wherein X represents OH can be prepared by oxidation of an appropriate 21-hydroxy-20-keto-pregnane of formula (VIII)

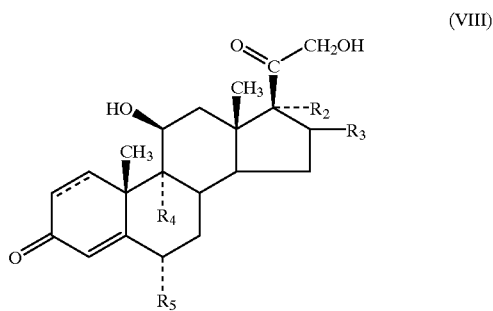

(VIII)

(in which $R_2$, $R_3$, $R_4$, $R_5$ and ══ are as defined hereinbefore) using, for example, the methodology described by Kertesz and Marx, Journal of Organic Chemistry, 1986, 51, 2315–2328.

Compounds of formula (VIII) are commercially available, for example, fluocinolone acetonide, budesonide and triamcinolone acetonide are available from Sigma-Aldrich, or can be prepared from the commercially available compounds of formula (VIII) by, for example, the transacetalisation methods described in EP0262108 and by partial reduction of the 1,2 double bond compounds by the methods described herein. Alternatively, compounds of formula (VIII) can be prepared from commercially available 17α-hydroxyl derivatives of compounds of formula (VIII), for example, betamethasone, flumethasone prednisolone, beclomethasone, and dexamethasone available from Sigma-Aldrich, by esterification of the 17α-hydroxyl group according to the method described by Gardi et al, Tetrahedron Letters, 1961, 448. Novel compounds of formula (VIII) form yet a further aspect of the present invention.

Compounds of formula (II) wherein X represents SH can be prepared by the application or adaptation of known methods, for example, using methods described by Phillipps et al, Journal of Medicinal Chemistry, 1994, 37, 3717–3729.

Compounds of formula (III), (VI) and (VII) are commercially available from Sigma-Aldrich or may be readily prepared by application or adaptation of known methods. For example, compounds of formula (III) wherein Z is SH can be prepared by methods described in G. Fuchs in Ark-Kemi, 1966, 26, 111 and 1968, 29, 379; compounds of formula (III) wherein Z is β-amino can be prepared by the methods described in G. J. McGarvey et al. Tetrahedron Letters, 1983, 24, 2733; the chiral α-OH compounds of formula (III) can be prepared by the methods described in Kenne et al. J. Chem. Soc. Perkin Trans. I, 1988, 1183; and the α-chloro compound of formula (VI) by the methods described in P Four et al, J. Org. Chem. 1981, 46, 4439.

Individual isomers of formula (I) at the point of attachment of the lactone moiety may either be prepared from starting materials having the desired stereochemistry or by epimerisation, resolution fractional crystallisation or chromatography (e.g. HPLC separation) at an appropriate stage in the synthesis of the required compounds of formula (I) using conventional means.

Thus, for example, it will be appreciated that synthesis employing a racemic mixture of compounds of formula (III) or (VI) will afford compounds of formula (I) as a mixture of diastereoisomers, which may then be separated. Alternatively, the individual diastereoisomers may be prepared by employing compounds of formula (III) or (VI) in enantiomerically pure form.

Similarly, compounds of formula (I) in which $R_2$ and $R_3$ together represent

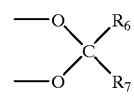

wherein $R_6$ and $R_7$ are different, may exist in the R and S diastereoisomeric forms. Synthesis of such compounds may be stereospecific to yield individual diastereoisomers. Thus, for example, the R-diastereoisomer of a compound of formula (I) wherein $R_6$ represents H and $R_7$ represents n-propyl may be conveniently prepared by transacetalisation of the corresponding 16α,17α-isopropylidenedioxy derivative with butyraldehyde in the presence of an acid catalyst, such as perchloric acid, as described in EP0262108. The transacetalisation reaction may be performed at an intermediate stage or after introduction of the lactone group.

Solvates (e.g. hydrates) of a compound of formula (I) may be formed during work-up procedure of one of the aforementioned process steps. Thus, the compounds of formula (I) may be isolated in association with solvent molecules by crystallisation from or evaporation of an appropriate solvent to give the corresponding solvates.

The following Examples illustrate the invention but do not limit the invention in any way.

EXAMPLES

General

Melting points were determined on a Kofler block and are uncorrected. $^1$H-nmr spectra were recorded at 250 or 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), dt (doublet of triplets) and b (broad). MS(TSP+ve) and MS(ES+ve) refer to mass spectra run in positive mode using thermospray or electrospray techniques respectively. HRMS (ES+ve) refers to high resolution eiectrospray mass spectrum run in positive mode. TLC (thin layer chromatography) was performed on Merck Kieselgel 60

Intermediate 1
6α,9α-Difluoro-11β-hydroxy-16α-methyl-3-oxo-17α-propionyloxy-androst-4-ene-17β-carboxylic acid 6α,9α-Difluoro-11β-hydroxy-16α-methyl-3-oxo-17α-propionyloxy-androsta-1,4-diene-17β-carboxylic acid (1.36 g, 3 mmol) was added to a solution of Wilkinson's catalyst (150 mg) in ethyl acetate (100 ml) and the resultant solution stirred under an atmosphere of hydrogen until hydrogenation was complete. The progress of the reaction was followed by HPLC. The solution was then extracted with saturated aqueous sodium bicarbonate (4×50 ml) and the combined aqueous layers washed with ethyl acetate (75 ml) before acidification of the aqueous layer to pH1 with conc. hydrochloric acid. This was then extracted with ethyl acetate (75 ml) and the extract dried and evaporated to yield the title compound as a solid (1.14 g, 84%): mp. 216–218° C.; MS (TSP+ve) m/z 455 [MH]$^+$; NMR δ (DMSO d$_6$) includes 12.50 (1H, bs), 5.80 (1H, s), 5.60 and 5.40 (1H, 2m), 5.13 (1H, m), 3.18 (1H, m), 2.34 (2H, q, J 8 Hz), 1.48 (3H, s), 1.00 (6H, s and t, J 8 Hz), 0.85 (3H, d, J 9 Hz).

Intermediate 2
6α,9α-Difluoro-11β-hydroxy-16α-methyl-3-oxo-17α-propionyloxy-androst-4-ene-17β-carbothioic acid S-(N,N-dimethylcarbamic acid anhydride)

Triethylamine (378 μl, 2.72 mmol) was added to a suspension of 6α,9α-difluoro-11β-hydroxy-16α-methyl-3-oxo-17α-propionyloxy-androst-4-ene- 17β-carboxylic acid, (Intermediate 1, 825 mg, 1.81 mmol) in dry dichloromethane (12 ml) under nitrogen. A clear solution was obtained and N,N-dimethylthiocarbamoyl chloride (669 mg, 5.43 mmol) was then added in one portion, the solution stirred at room temperature and progress of the reaction followed by HPLC. On completion the reaction was diluted with ethyl acetate (50 ml) and washed successively with 1M hydrochloric acid (30 ml), 5% sodium bicarbonate solution (30 ml) and brine solution (30 ml) before drying and evaporating to yield the crude product as a foam. This was purified by preparative layer chromatography on silica gel, eluting with dichloromethanediethyl ether (5:2) to give the title compound as a crystalline solid (507 mg, 58%): mp. 189–191° C.; IR ν$_{max}$ (KBr) 3363, 1750, 1722, 1669, 1651 cm$^{-1}$; NMR δ (CDCl$_3$) includes 6.13 (1H, s), 5.20 and 5.35 (1H, 2m), 4.37 (1H, m), 3.33 (1H, m), 3.08 and 3.16 (6H, 2s), 2.42 (2H, q, J 7 Hz), 1.51 (3H, s), 1.14–1.20 (6H, s and t, J 7 Hz), 0.98 (3H, d, J 7 Hz). Found: C, 59.53; H, 7.11; N, 2.40; S, 5.69. C$_{27}$H$_{37}$F$_2$NO$_6$S requires C, 59.87; H, 6.89; N, 2.59; S, 5.92%).

Intermediate 3
6α,9α-Difluoro-11β-hydroxy-16α-methyl-3-oxo-17α-propionyloxy-androst-4-ene-17β-carbothioic acid A mixture of 6α,9α-difluoro-11β-hydroxy-16α-methyl-3-oxo-17α-propionyloxy-androst-4-ene-17β-carbothioic acid S-(N,N-imethylcarbamic acid anhydride) (Intermediate 2, 490 mg, 0.905 mmol) in diethylamine (5 ml) was heated under reflux in a nitrogen atmosphere. The progress of the reaction was followed by TLC analysis and when complete the reaction mixture was poured into an ice-cooled mixture of 3.5M hydrochloric acid (60 ml) and ethyl acetate (40 ml). The organic phase was separated, washed with water (30 ml) and extracted with 5% sodium carbonate solution (3×20 ml). The combined basic extracts were then layered with ethyl acetate (40 ml) and adjusted to pH1 with 6M hydrochloric acid. The organic phase was separated, dried and evaporated to give the title compound as a solid (190 mg, 45%): mp. 147–151° C.; MS (TSP+ve) m/z 471 [MH]$^+$; NMR δ (CDCl$_3$) includes 6.13 (1H, s), 5.38 and 5.19 (1H, 2m), 4.40 (1H, m), 3.28 (1H, m), 2.43 (2H, q, J 7 Hz), 1.52 (3H, s), 1.17 (3H, t, J 7 Hz) 1.13 (3H, s), 0.99 (3H, d, J 7 Hz).

Intermediate 4
Methanesulfonic acid 2-oxo-tetrahydro-furan-3R-yl ester

To a stirring solution of (R)-3-hydroxy-2-oxo-tetrahydro-furan (400 mg, 3.92 mmol) and triethylamine (601 μl, 4.31 mmol) in anhydrous dichloromethane (15 ml) at 0° C. under a nitrogen atmosphere was added methanesulfonyl chloride (334 μl, 4.31 mmol). The resulting mixture was stirred at 0° C. for 0.25 h and at 21° C. for 2.5 h. Further quantities of triethylamine (109 μl, 0.78 mmol) and methanesulfonyl chloride (61 μl, 0.78 mmol) were added and the mixture stirred for 1.5 h. The reaction mixture was poured into water (20 ml) and the separated aqueous layer was extracted with dichloromethane (20 ml). The combined organic layers were washed with saturated sodium bicarbonate solution (20 ml) and saturated brine (20 ml) then dried over anhydrous magnesium sulfate. The solvent was removed under reduced pressure yielding a yellow residue which was purified by flash column chromatography on silica gel using ethyl acetate:cyclohexane (3:2) as eluent. Removal of the solvent from appropriate fractions under reduced pressure gave the title compound as a white crystalline solid (214 mg, 30%): mp 69–72° C.; MS (TSP+ve) m/z 198 (M+NH$_4$)$^+$; IR ν$_{max}$ (KBr) 1774, 1363 cm$^{-1}$; NMR δ (CDCl$_3$) 5.33 (1H, t, J 9 Hz), 4.53 (1H, dt, J 9 and 3.5 Hz), 4.43–4.28 (1H, m), 3.30 (3H, s), 2.88–2.72 (1H, m), 2.66–2.47 (1H, m). (Found: C, 33.53; H, 4.16; S, 17.35. C$_5$H$_8$O$_5$S.0.05H$_2$O requires C, 33.17; H, 4.51; S, 17.71%).

Intermediate 5
Methanesulfonic acid 2-oxo-tetrahydro-furan-3S-yl ester

Methanesulfonyl chloride (1.67 ml, 21.56 mmol) was added to a stirred solution of (S)-3-hydroxy-2-oxo-tetrahydrofuran (2 g, 19.6 mmol), 4-N,N-dimethylaminopyridine (240 mg, 1.96 mmol) and diisopropylethylamine (3.76 ml, 21.56 mmol) in dry dichloromethane (20 ml), under nitrogen, at −40° C. The mixture was stirred for 30 minutes and then allowed to warm up to room temperature, then it was washed with 2M hydrochloric acid solution (50 ml), dried and evaporated to a solid. The crude product was purified by flash chromatography on silica gel, eluting with ethyl acetate-cyclohexane (1:1). Trituration with diethylether and drying in vacuo afforded the title compound as a crystalline white solid (2.23 g, 63%): mp. 70–75° C.; NMR δ (CDCl$_3$) 5.33 (1H, t, J 8 Hz), 4.53 (1H, dt, J 9 and 2 Hz), 4.34 (1H, dt, J 10 and 6 Hz), 3.28 (3H, s), 2.86–2.72 (1H, m), 2.65–2.47 (1H, m).

Intermediate 6
16α,17α-(R-Butylidenedioxy)-6α,9α-difluoro-11β-hydroxy-3-oxo-androst-4-ene-17β-carbothioic acid S-(N,N-dimethylcarbamic acid anhydride)

Triethylamine (550 ∞l, 3.94 mmol) was added to a suspension of 16α,17α-(R-butylidenedioxy)-6α,9α-difluoro-11β-hydroxy-3-oxo-androst-4-ene-17β-carboxylic acid (1.345 g, 2.96 mmol) in dry dichloromethane (20 ml) under nitrogen. A clear solution was obtained and N,Ndimethylthiocarbamoyl chloride (1.11 g, 9 mmol) was then added in one portion, the solution stirred at room temperature and progress of the reaction followed by HPLC. On completion the reaction mixture was concentrated under reduced pressure and the residue was dissolved in ethyl acetate (50 ml) and washed successively with 2M hydrochloric acid (30 ml), 5% sodium bicarbonate solution (30 ml) and brine solution (30 ml) before drying and evaporating to yield the crude product as a foam. This was purified by column chromatography on silica gel, eluting with acetone-dichloromethane (1:9) to give the title compound as a foam (840 mg, 52%): MS (ES+ve) m/z 542 (MH)$^+$; NMR δ (CDCl$_3$) includes 6.15 (1H, s), 5.37 and 5.18 (1H, 2m), 4.86 (1H, d, J 5 Hz), 4.78 (1H, t, J 4 Hz), 4.40 (1H, m), 3.14 and 3.09 (6H, 2s), 1.52 (3H, s), 1.04 (3H, s), 0.96 (3H, d, J 7 Hz).

Intermediate 7

16α,17α-(R-Butylidenedioxy)-6α,9α-difluoro-11β-hydroxy-3-oxo-androst-4-ene-17β-carbothioic acid A mixture of 16α,17α-(R-butylidenedioxy)-6α,9α-difluoro-11β-hydroxy-3-oxo-androst-4-ene-17β-carbothioic acid S-(N,N-dimethylcarbamic acid anhydride (Intermediate 6; 830 mg, 1.53 mmol) in diethyiamine (8 ml) was heated under reflux in a nitrogen atmosphere. The progress of the reaction was followed by TLC analysis and when complete the reaction mixture was concentrated under reduced pressure and the residue was dissolved in ethyl acetate (50 ml) and acidified 2M hydrochloric acid (40 ml). The organic phase was separated, washed with water (30 ml) and extracted with 5% potassium carbonate solution (5×20 ml). The combined basic extracts were then layered with ethyl acetate (40 ml) and adjusted to pH1 with 6M hydrochloric acid. The organic phase was separated, dried and evaporated to give the title compound as a foam (103 mg, 14%): MS (ES−ve) m/z 469 [M−H]$^−$; NMR δ (CDCl$_3$) includes 6.15 (1H, s), 5.38 and 5.18 (1H, 2m), 4.94.7 (2H, m), 4.40 (1H, m), 1.52 (3H, s), 1.03 (3H, s), 0.96 (3H, t, J 7 Hz).

Example 1

6α,9α-Difluoro-11β-hydroxy-16α-methyl-3-oxo-17α-propionyloxy-androsta-1,4-diene-17β-carbothioic acid S-(2-oxo-tetrahydro-furan-3-yl) ester.

Powdered anhydrous potassium carbonate (76 mg, 0.55 mmol) was added to a stirred solution of 6α,9α-difluoro-11β-hydroxy-16α-methyl-3-oxo-17α-propionyloxy-androsta-1,4-diene-17β-carbothioic acid (258 mg, 0.55 mmol) in dry DMF (4 ml). The mixture was stirred under nitrogen and then cooled in ice. α-Bromo-γ-butyrolactone (56 μl, 0.68 mmol) was then added and the mixture stirred until reaction was complete as monitored by TLC. The solution was partitioned between water (25 ml) and ethyl acetate (25 ml).

The organic phase was separated, washed with water (2×25 ml) dried and evaporated to a solid. The crude product was purified by flash column chromatography on silica gel using initially ether and finally ethyl acetate as eluant, isolating the title compound isomer A as a crystalline solid (120 mg, 39.5%): mp. 237–238° C.; MS (TSP+ve) m/z 553 [MH]$^+$; IR ν$_{max}$ (KBr) 1768, 1739, 1671, 1633 cm$^{-1}$; NMR δ (CDCl$_3$) includes 7.17 (1H, d, J 10 Hz), 6.42 (1H, bs), 6.38 (1H, d, J 10 Hz), 5.49 and 5.39 (1H, 2m), 4.50–4.10 (4H, m), 3.31 (1H, m), 2.36 (2H, q, J 7.5 Hz), 1.53 (3H, s), 1.15 (3H, s), 1.13 (3H, t, J 7.5 Hz), 0.99 (3H, d, J 6.25 Hz). (Found: C, 60.72; H, 6.39; S, 5.58. C$_{28}$H$_{34}$F$_2$O$_7$S requires C, 60.85; H, 6.30; S, 5.80%) and the title compound isomer B as a crystalline solid (116 mg, 38.2%): mp. 220–222° C.; MS (TSP+ve) m/z 553 [MH]$^+$; IR ν$_{max}$ (KBr) 1769, 1740, 1678, 1633 cm$^{-1}$; NMR δ (CDCl$_3$) includes 7.16 (1H, d, J 10 Hz), 6.43 (1H, bs), 6.38 (1H, d, J 10 Hz), 5.49 and 5.39 (1H, 2m), 4.62–4.32 (3H, m), 4.06 (1H, m), 3.32 (1H, m), 1.53 (3H, s), 1.12 (6H, m), 0.98 (3H, d, J 6.25 Hz). (Found: C, 60.96; H, 6.28; S, 5.70. C$_{28}$H$_{34}$F$_2$O$_7$S requires C, 60.85; H, 6.20; S, 5.80%).

Example 2

6α,9α-Difluoro-11β-hydroxy-16α-methyl-3-oxo-17α-propionyloxy-androsta-1,4-diene-17β-carbothioic acid S-(2-oxo-tetrahydro-furan-3S-yl)-ester.

Method 1

Triphenylphosphine (168 mg, 0.64 mmol) was added to a solution of diisopropylazodicarboxyiate (0.126 ml, 0.64 mmol) in tetrahydrofuran (3 ml) stirred at 0° C. under nitrogen. After formation of a yellow precipitate a solution of 6α,9α-difluoro-11α-hydroxy-16-methyl-3-oxo-17α-propionyloxy-androsta-1,4-diene-17β-carbothioic acid (200 mg, 0.43 mmol) and (R)-α-hydroxy-γ-butyrolactone (65 mg, 0.64 mmol) in tetrahydrofuran (3 ml) was added and the progress of the reaction followed by TLC analysis. On completion the solvent was removed and the residue absorbed directly onto silica gel and purified by flash column chromatography, eluting with diethyl ether. The title compound was isolated as a white crystalline solid (149 mg, 63%): mp. 236–238° C.; analytical and spectroscopic data were identical to that obtained previously for isomer A of Example 1.

Method 2

Methanesulfonic acid 2-oxo-tetrahydro-furan-3R-yl ester (Intermediate 4, 93 mg, 0.52 mmol) was treated with a solution of 6α,9β-difluoro-11β-hydroxy-16α-methyl-3-oxo-17α-propionyloxy-androsta-1,4-diene-17β-carbothioic acid sodium salt (253 mg, 0.52 mmol) in DMF (3 ml) and the mixture was stirred at 20° C. under nitrogen for 2.5 h. The progress of the reaction was followed by TLC analysis. On completion the reaction mixture was diluted with ethyl acetate and poured into water. The organic solution was washed with sodium bicarbonate, 2 M hydrochloric acid, brine, dried and evaporated to dryness to give the title compound (246 mg, 86%): mp. 237–238° C.; spectroscopic data were identical to that obtained previously for isomer A of Example 1.

Example 3

6α,9α-Difluoro-11β-hydroxy-16α-methyl-3-oxo-17α-propionyloxy-androsta-1,4-diene-17β-carbothioic acid S-(2-oxo-tetrahydro-furan-3R-yl) ester.

Triphenylphosphine (168 mg, 0.64 mmol) was added to a solution of diisopropylazodicarboxylate (0.126 ml, 0.64 mmol) in tetrahydrofuran (3 ml) stirred at 0° C. under nitrogen. After formation of a yellow precipitate a solution of 6α,9α-difluoro-11β-hydroxy-16α-methyl-3-oxo-17α-propionytoxy-androsta-1,4-diene-17β-carbothioic acid (200 mg, 0.43 mmol) and (S)-α-hydroxy-γ-butyrolactone (65 mg, 0.64 mmol) in tetrahydrofuran (3 ml) was added and the progress of the reaction followed by TLC analysis. On completion the solvent was removed and the residue absorbed directly onto silica gel and purified by flash column chromatography, eluting with diethyl ether. The title compound was isolated as a white crystalline solid (143 mg, 61%): mp. 219–222° C.; analytical and spectroscopic data were identical to that obtained previously for isomer B of Example 1.

Example 4
6α,9α-Difluoro-11β-hydroxy-16α-methyl-3-oxo-17α-propionytoxy-androst-4-ene-17β-carbothioic acid S-(2-oxo-tetrahydro-furan-3-yl) ester.

Powdered anhydrous potassium carbonate (102 mg, 0.735 mmol) was added to a stirred solution of 6α,9β-difluoro-11β-hydroxy-16α-methyl-3-oxo-17α-propionyloxy-androst-4-ene-17β-carbothioic acid (Intermediate 3, 346 mg, 0.735 mmol) in dry DMF (5 ml). The mixture was stirred under nitrogen and then cooled in ice. α-Bromo-γ-butyrolactone (70 µl, 0.85 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by flash column chromatography on silica gel using initially ether and finally ethyl acetate as eluant, isolating the title compound isomer A as a crystalline solid (85 mg, 20%): mp. 244–246° C.; MS (TSP+ve) m/z 572 [MNH$_4$]$^+$; IR $\nu_{max}$ (KBr) 1773, 1742 cm$^{-1}$; NMR δ (CDCl$_3$) includes 6.14 (1H, s), 5.37 and 5.18 (1H, 2m), 4.52 (1H, m), 4.43-4.28 (2H, m), 4.18 (1H, m), 3.33 (1H, m), 2.75 (1H, m), 2.40 (2H, q, J 7 Hz), 1.52 (3H, s), 1.13 (3H, t, J 7 Hz), 1.12 (3H, s), 1.01 (3H, d, J 7 Hz) (Found: C, 60.33; H, 6.74; S, 5.70, C$_{28}$H$_{36}$F$_2$O$_7$S requires C, 60.63; H, 6.54; S, 5.78%) and the title compound isomer B as a crystalline solid (80 mg, 20%): mp. 195–197° C.; MS (TSP+ve) m/z 572 [MNH$_4$]$^+$; IR $\nu_{max}$ (KBr) 1770, 1747 cm$^{-1}$; NMR δ (CDCl$_3$) includes 6.07 (1H, s), 5.30 and 5.11 (1H, 2m), 4.49 (1H, m), 4.37–4.24 (2H, m) 3.96 (1H, m), 3.36 (1H, m), 2.64 (1H, m), 2.34 (2H, q, J 7 Hz), 1.44 (3H, s), 1.08 (3H, t, J 7 Hz), 1.04 (3H, s), 0.93 (3H, d, J 7 Hz) (Found: C, 60.34; H, 6.60; S, 5.63. C$_{28}$H$_{36}$F$_2$O$_7$S require C, 60.63; H, 6.54; S, 5.78%).

Example 5
17α-Butyryloxy-6α,9α-difluoro-11β-hydroxy-16α-methyl-3-oxo-androsta-1,4-diene-17β-carbothioic acid S-(2-oxo-tetrahydro-furan-3-yl) ester.

Powdered anhydrous potassium carbonate (59 mg, 0.43 mmol) was added to a stirred solution of 17α-butyryloxy-6α,9α-difluoro-11β-hydroxy-16α-methyl-3-oxo-androsta-1,4-diene-17β-carbothioic acid (206 mg, 0.43 mmol) in dry DMF (3 ml). The mixture was stirred under nitrogen and then cooled in ice. α-Bromo-γ-butyrolactone (46 µl, 0.53 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative layer chromatography on silica gel eluting with chloroform-ethyl acetate (2:1), to give the title compound isomer A as a crystalline solid: (30.7 mg, 13%) mp. 143–145° C.; MS (TSP+ve) m/z 567 [MH]$^+$; IR $\nu_{max}$ (KBr) 1772, 1741, 1669, 1629 cm$^{-1}$; NMR δ (CDCl$_3$) includes 7.14 (1H, d, J 10 Hz), 6.42 (1H, s), 6.39 (1H, d, J 10 Hz), 5.49 and 5.29 (1H, 2m), 4.50 (1H, m), 4.39 (2H, m), 4.31 (1H, m), 4.13 (1H, m), 3.32 (1H, m), 2.75 (1H, m), 1.54 (3H, s), 1.16 (3H, s), 1.00 (3H, d, J 6.25 Hz), 0.95 (3H, t, J 7.25 Hz); (Found: C, 60.87; H, 6.40; S, 5.42. C$_{29}$H$_{36}$FO$_7$S. 0.4 H$_2$O requires C, 60.70; H, 6.46; S, 5.59%) and the title compound isomer B as a crystalline solid (46 mg, 19%): mp. 164–166° C.; MS (TSP+ve) m/z 567 [MH]$^+$; IR $\nu_{max}$ (KBr) 1771, 1743, 1668, 1630 cm$^{-1}$; NMR δ (CDCl$_3$) includes 7.14 (1H, d, J 10 Hz), 6.43 (1H, s), 6.39 (1H, d, J 10 Hz), 5.49 and 5.30 (1H, 2m), 4.55 (1H, m), 4.39 (2H, m), 4.09 (1H, m), 3.31 (1H, m), 2.70 (1H, m), 1.53 (3H, s), 1.14 (3H, s), 0.95 (6H, d, J 6.25 Hz and t, J 7.25 Hz); HRMS (ES+ve) found 567.2200, [MH]$^+$. C$_{29}$H$_{37}$F$_2$O$_7$S requires 567.2205.

Example 6
17α-Acetyloxy-α,9α-difluoro-11β-hydroxy-16α-methyl-3-oxo-androsta-1,4-diene-17β-carbothioic acid S-(2-oxo-tetrahydro-furan-3-yl) ester.

Powdered anhydrous potassium carbonate (55 mg, 0.40 mmol) was added to a stirred solution of 17α-acetyloxy-6α,9α-difluoro-11β-hydroxy-16α-methyl-3-oxo-androsta-1,4-diene-17β-carbothioic acid (181 mg, 0.40 mmol) in dry DMF (3 ml). The mixture was stirred under nitrogen and then cooled in ice. α-bromo-γ-butyrolactone (43 µl, 0.50 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative layer chromatography on silica gel eluting with chloroform:cyclohexane:ethanol (10:10:1), to give the title compound isomer A as a crystalline solid (74 mg, 34%): mp. 253–255° C.; MS (TSP+ve) m/z 539 [MH]$^+$; IR $\nu_{max}$ (KBr) 1766, 1750, 1669, 1631 cm$^{-1}$; NMR δ (CDCl$_3$) includes 7.13 (1H, d, J 10 Hz), 6.43 (1H, s), 6.38 (1H, d, J 10 Hz), 5.49 and 5.28 (1H, 2m), 4.50 (1H, m), 4.37 (2H, m), 4.13 (1H, m), 3.30 (1H, m), 2.74 (1H, m), 2.06 (3H, s), 1.54 (3H, s), 1.18 (3H, s), 1.00 (3H, d, J 7 Hz). (Found: C, 58.81; H, 5.88; S, 5.78. C$_{27}$H$_{32}$F$_2$O$_7$S.0.7 H$_2$O requires C, 58.83; H, 6.11; S, 5.82%) and the title compound isomer B as a crystalline solid (74 mg, 34%): mp. 258–260° C.; MS (TSP+ve) m/z 539 [MH]$^+$; IR $\nu_{max}$ (KBr) 1772, 1752, 1668, 1630 cm$^{-1}$; NMR δ (CDCl$_3$) includes 7.13 (1H, d, J 10 Hz), 6.43 (1H, bs), 6.39 (1H, d, J 10 Hz), 5.49 and 5.29 (1H, 2m), 4.56 (1H, m), 4.40 (2H, m), 4.10 (1H, m), 3.70 (1H, m), 3.31 (1H, m), 2.10 (3H, s), 1.55 (3H s), 1.15 (3H, s) 1.00 (3H, d, J 7 Hz). (Found: C, 58.76; H, 5.77; S, 5.71. C$_{27}$H$_{32}$F$_2$O$_7$S 0.7 H$_2$O requires C, 58.83; H, 6.11; S, 5.82%)

Example 7
9α-Fluoro-11β-hydroxy-16β-methyl-3-oxo-17α-propionyloxy-androsta-1,4-diene-17β-carbothioic acid S-(2-oxo-tetrahydro-furan-3-yl) ester.

Powdered anhydrous potassium carbonate (76 mg, 0.55 mmol) was added to a stirred solution of 9α-fluoro-11β-hydroxy-16β-methyl-3-oxo-17α-propionyloxy-androsta-1,4-diene-17β-carbothioic acid (352 mg, 0.75 mmol) in dry DMF (7 ml). The mixture was stirred under nitrogen and then cooled in ice. α-Bromo-γ-butyrolactone (78 µl, 0.94 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by flash column chromatography on silica gel using initially ether and finally ethyl acetate as eluant, isolating the title compound isomer A as a crystalline solid (124 mg, 30%): MS (TSP+ve) m/z 535 [MH]$^+$; HRMS (ES+ve) found: 535.2169 [MH]$^+$, C$_{29}$H$_{36}$FO$_7$S requires 535.2164; IR $\nu_{max}$ (nujol) 3443, 1772, 1742, 1716, 1663, 1621, 1605 cm$^{-1}$; NMR δ (CDCl$_3$) includes 7.22 (1H, d, J 10 Hz), 6.36 (1H, d, J 10 Hz), 6.14 (1H, bs), 4.49–4.28 (4H, m), 2.80 (1H, m), 2.37 (2H, q, J 7.5 Hz), 1.56 (3H, s), 1.42 (3H, d, J 6.25 Hz), 1.14 (3H, t, J 7.5 Hz), 1.06 (3H, s). (Found: C, 61.90; H 6.69; S, 5.83. C$_{28}$H$_{35}$FO$_7$S.0.45 H$_2$O requires C, 61.97; H, 6.67; S, 5.91%) and the title compound isomer B as a crystalline solid (156 mg, 37%): MS (TSP+ve) m/z 535 [MH]$^+$; HRMS (ES+ve) found: 535.2165 [MH]$^+$. C$_{29}$H$_{36}$FO$_7$S requires 535.2164; IR $\nu_{max}$ (nujol) 3461, 1771, 1743,1707, 1658, 1614 cm$^{-1}$; NMR δ (CDCl$_3$) includes 7.22 (1H, d, J 10 Hz), 6.35 (1H, d, J 10 Hz), 6.13 (1H, bs), 4.61 (1H, m), 4.42 (1H, m), 4.34 (1H, m), 3.69 (1H, m), 2.82 (1H, m), 2.37 (2H, q, J 7.5 Hz), 1.55 (3H, s), 1.38 (3H, d, J 6.25 Hz), 1.15 (3H, t, J 7.5 Hz), 1.01 (3H, s). (Found: C, 61.51; H, 6.72; S, 5.61. $C_{28}H_{35}FO_7S.0.6\ H_2O$ requires C, 61.34; H, 6.71; S, 5.85%).

Example 8

6α,9α-Difluoro-11β-hydroxy-16α-methyl-3-oxo-17α-propionyloxy-androsta-1,4-diene-11β-carbothioic acid S-(5-oxo-tetrahydro-furan-2-yl) ester.

Powdered anhydrous potassium carbonate (76 mg, 0.55 mmol) was added to a stirred solution of 6α,9α-difluoro-11β-hydroxy-16α-methyl-3-oxo-17α-propionyloxy-androsta-1,4-diene-17β-carbothioic acid (258 mg, 0.55 mmol) in dry DMF (5 ml). The mixture was stirred under nitrogen and then cooled in ice. γ-Chloro-γ-butyrolactone (69 μl, 0.69 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative layer chromatography on silica gel, eluting with chloroform-cyclohexane-ethanol (20:20:1), to give the title compound isomer A as a crystalline solid (50 mg, 16%): mp. 152° C.; MS (TSP+ve) m/z 553 [MH]$^+$; IR $v_{max}$ (KBr) 3459, 1791, 1742, 1704, 1667, 1631 cm$^{-1}$; NMR δ (DMSO d$_6$) includes 7.13 (1H, d, J 10 Hz), 6.44 (1H, s), 6.39 (1H, d, J 10 Hz), 6.28 (1H, m), 5.48 and 5.28 (1H, 2m), 4.41 (1H, m), 3.41 (1H, m), 2.38 (2H, q, J 7 Hz), 1.52 (3H, s), 1.14 (3H, t, J 7 Hz), 1.14 (3H, s), 1.01 (3H, d, J 7 Hz); HRMS (ES+ve) found: 553.6446 [MH]$^+$, $C_{28}H_{35}F_2O_7S$ requires 553.6445, and the title compound isomer B as a crystalline solid (34 mg, 10%): mp. 210–213° C.; MS (TSP+ve) m/z 553 [MH]$^+$; IR $v_{max}$ (KBr) 1787, 1743, 1669, 1632 cm$^{-1}$; NMR δ (CDCl$_3$) includes 7.13 (1H, d, J 10 Hz), 6.44 (1H, d, J 10 Hz), 6.38 (1H, s), 6.24 (1H, m) 5.48 and 5.28 (1H, 2m), 4.40 (1H, m), 3.32 (1H, m), 2.36 (2H, q, J 7 Hz), 1.52 (3H, s), 1.16 (3H, m), 1.12 (3H, t, J 7 Hz), 1.02 (3H, d, J 7 Hz); HRMS (ES+ve) found 553.6445 [MH]$^+$, $C_{28}H_{35}F_2O_7S$ requires 553.6445.

Example 9

6α,9α-Difluoro-11α-hydroxy-16α-methyl-3-oxo-17α-propionyloxy-androsta-1,4-diene-17β-carbothioic acid S-(2-oxo-tetrahydro-furan-4-yl) ester.

Powdered anhydrous potassium carbonate (69 mg, 0.5 mmol) was added to a stirred solution of 6α,9α-difluoro-11β-hydroxy-16α-methyl-3-oxo-17α-propionyloxy-androsta-1,4-diene-17β-carbothioic acid (234 mg, 0.5 mmol) in dry DMF (2.5 ml). The mixture was stirred under nitrogen and then cooled in ice. 2(5H)-Furanone (400 μl, 5.63 mmol) was then added and the mixture stirred until reaction was complete as monitored by TLC. The solution was partitioned between water (25 ml) and ethyl acetate (25 ml). The organic phase was separated, washed with water (2×25 ml) dried and evaporated to a solid. The crude product was purified by preparative layer chromatography on silica gel using ethyl acetate as eluant, isolating the title compound as a crystalline solid (9 mg, 3%): MS (FAB+ve) m/z 553 [MH]$^+$; IR $v_{max}$ (KBr) 3474, 1784, 1745, 1667, 1633 cm$^{-1}$; NMR δ (CDCl$_3$) includes 7.13 (1H, d, J 10 Hz), 6.45 (1H, s), 6.38 (1H, d, J 10 Hz), 5.48 and 5.28 (1H, 2m), 4.80–4.67 (1H, m), 4.41 (1H, m), 4.35–4.2 (2H, m), 3.29 (1H, m), 3.05 (0.5H, dd, J 9 and 4 Hz), 2.98 (0.5H, dd, J 9 and 4 Hz), 2.59 (0.5H, t, J 5 Hz), 2.52 (0.5H, t, J 5 Hz), 2.47 (3H, q, J 8 Hz), 1.54 (3H, s), 1.05–1.27 (6H, m), 0.97 and 0.98 (3H, 2d, J 8 Hz); HRMS (ES+ve) found: 553.2083 [MH]$^+$, $C_{28}H_{35}F_2O_7S$ requires 553.2072;

Example 10

6α,9α-Difluoro-11α-hydroxy-16α-methyl-3-oxo-17α-propionyloxy-androsta-1,4-diene-17β-carboxyiic acid (2-oxo-tetrahydro-furan-3-yl) ester.

Powdered anhydrous potassium carbonate (103 mg, 0.75 mmol) was added to a stirred solution of 6α,9α-difluoro-11β-hydroxy-16α-methyl-3-oxo-17α-propionyloxy-androsta-1,4-diene-17β-carboxylic acid (340 mg, 0.75 mmol) in dry DMF (7 ml). The mixture was stirred under nitrogen and then cooled in ice. α-Bromo-γ-butyrolactone (78 μl, 0.94 mmol) was then added and the mixture stirred until reaction was complete as monitored by TLC. The solution was partitioned between water (25 ml) and ethyl acetate (25 ml). The organic phase was separated, washed with water (2×25 ml) dried and evaporated to a solid. The crude product was purified by preparative layer chromatography on silica gel, eluting with chloroform-cyclohexane-ethanol (20:20:1), to give the title compound isomer A as a crystalline solid (43 mg, 11%): mp. 205–206° C.; MS (TSP+ve) m/z 537 [MH]$^+$; IR $v_{max}$ (KBr) 3443, 1786, 1747, 1669, 1632, 1612 cm$^{-1}$; NMR δ (CDCl$_3$) includes 7.27 (1H, d, J 10 Hz), 6.29 (1H, d, J 10 Hz), 6.11 (1H, s), 5.68 (1H, m), 5.70 and 5.55 (1H, 2m), 4.33–4.22 (2H, m), 4.16 (1H, m), 3.21 (1H, m), 2.35 (2H, q, J 7 Hz), 1.48 (3H, s), 1.04 (3H, s), 1.00 (3H, t, J 7 Hz), 0.86 (3H, d, J 7 Hz); HRMS (ES+ve) found: 537.2295 [MH]$^+$, $C_{28}H_{35}F_2O_8$ requires 537.2294, and the title compound isomer B as a crystalline solid (43 mg, 11%): mp. 231–233° C.; MS (TSP+ve) m/z 537 [MH]$^+$; IR $v_{max}$ (KBr) 3482, 1789, 1747, 1668, 1630 cm$^{-1}$; NMR δ (CDCl$_3$) includes 7.13 (1H, d, J 10 Hz), 6.41(1H, s), 6.39 (1H, d, J 10 Hz), 5.51 and 5.20 (1H, 2m), 5.10 (1H, m), 4.58 (1H, m), 4.46–4.32 (2H, m), 3.30 (1H, m), 2.40 (2H, q, J 7 Hz), 1.72 (3H, s), 1.55 (3H, s), 1.00 (3H, t, J 7 Hz), 0.96 (3H, d, J 7 Hz); HRMS (ES+ve) found: 537.2299 [MH]$^+$, $C_{28}H_{35}F_2O_8$ requires 537.2297.

Example 11

6α,9α-Difluoro-11β-hydroxy-16α-methyl-3-oxo-17α-propionyloxy-androsta-1,4-diene-17β-carboxylic acid (2-oxo-Aetrahydro-furan-5-yl) ester.

Powdered anhydrous potassium carbonate (76 mg, 0.55 mmol) was added to a stirred solution of 6α,9α-difluoro-11β-hydroxy-16α-methyl-3-oxo-17α-propionyloxy-androsta-1,4-diene-17β-carboxylic acid (249 mg, 0.55 mmol) in dry DMF (5 ml). The mixture was stirred under nitrogen and then cooled in ice. γ-Chloro-γ-butyrolactone (83 μl, 0.69 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative layer chromatography on silica gel, eluting with chloroform-cyclohexane-ethanol (20:20:1), to give the title compound isomer A as a crystalline solid (62 mg, 21%): mp. 263–266° C.; MS (TSP+ve) m/z 537 [MH]$^+$; HRMS (ES+ve) found: 537.5780 [MH]$^+$, $C_{28}H_{35}F_2O_8$ requires 537.5779; IR $v_{max}$ (KBr) 3459, 1789, 1733, 1669, 1633 cm$^{-1}$; NMR δ (DMSO d$_6$) includes 7.10 (1H, d, J 10 Hz), 6.69 (1H, m), 6.44 (1H, s), 6.38 (1H, d, J 10 Hz), 5.48 and 5.28 (1H, 2m), 4.37 (1H, m), 3.33 (1H, m), 2.37 (2H, q, J 7 Hz), 1.53 (3H, s), 1.13 (3H, t, J 7 Hz), 1.08 (3H, s), 0.93 (3H, d, J 7 Hz). (Found: C, 61.77; H, 6.15. $C_{28}H_{34}F_2O_7$ 0.3 $H_2O$ requires C, 62.05; H, 6.43%) and the title compound isomer B as a crystalline solid (48 mg, 16%): mp. 241–243° C.; MS (TSP+ve) m/z 537 [MH]$^+$; HRMS (ES+ve) found: 537.5788 [MH]$^+$, $C_{28}H_{35}F_2O_8$ requires 537.5779; IR $v_{max}$ (KBr) 3480, 1789, 1747, 1668, 1628 cm$^{-1}$; NMR δ (DMSO d$_6$) includes 7.12 (1H, d, J 10 Hz), 6.58 (1H, m), 6.43 (1H, s), 6.38 (1H, d, J 10 Hz), 5.48 and 5.28 (1H, 2m), 4.39 (1H, m), 3.22 (1H, m), 2.36 (2H, q, J 7 Hz), 1.53 (3H, s), 1.11 (3H, t, J 7 Hz), 1.10 (3H, s), 0.95 (3H, d, J 7 Hz). (Found: C, 61.69; H, 6.05. $C_{28}H_{34}F_2O_8$ 0.4 $H_2O$ requires C, 61.85; H, 6.45%).

Example 12

6α,9α-Difluoro-11β-hydroxy-16α,17α-isopropylidenedioxy-3-oxoandrosta-1,4-diene-17β-carbothioic acid S-(2-oxo-tetrahydro-furan-3-yl) ester.

Powdered anhydrous potassium carbonate (44 mg, 0.32 mmol) was added to a stirred solution of 6α,9α-difluoro-11β-hydroxy-16α,17α-isopropylidenedioxy-3-oxo-androsta-1,4-diene-17β-carbothioic acid (130 mg, 0.286 mmol) in dry DMF (1.4 ml). The mixture was stirred under nitrogen and then cooled in ice. α-Bromo-γ-butyrolactone (30 μl, 0.36 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative normal phase HPLC (Dynamax 60 Å C18, 25 cm×41 mm i.d.) eluting with 70–90% ethyl acetate/heptane at 45 ml/min with detection at 270 nm to give the title compound isomer A as a crystalline solid (29 mg, 20%): mp. 308–312° C.; MS (TSP+ve) m/z 539 [MH]$^+$; IR $\nu_{max}$ (KBr) 3310, 1778, 1694, 1668, 1629 cm$^{-1}$; NMR δ (DMSO d$_6$) includes 7.24 (1H, d, J 10 Hz), 6.30 (1H, d, J 10 Hz), 6.12 (1H, s), 5.73 and 5.52 (1H, 2m), 5.58 (1H, bs), 4.88 (1H, m), 4.47–4.15 (4H, m), 1.49 (3H, s), 1.37 (3H, s), 1.20 (3H, s), 0.90 (3H, s). (Found: C, 59.77; H, 6.01. $C_{27}H_{32}F_2O_7S$. 0.3 $H_2O$ requires C, 59.61; H, 6.04%) and the title compound isomer B as a crystalline solid (43 mg, 29%): mp. 275–278° C.; MS (TSP+ve) m/z 539 [MH]$^+$; IR $\nu_{max}$ (KBr) 3415, 2928, 1779, 1669, 1633 cm$^{-1}$; NMR δ (DMSO d$_6$) includes 7.25 (1H, d, J 10 Hz), 6.30 (1H. d, J 10 Hz), 6.11 (1H, s), 5.73 and 5.54 (1H, 2m), 5.57 (1H, m), 4.89 (1H, m), 4.48–4.16 4H, m), 1.50 (3H, s), 1.35 (3H, s), 1.20 (3H, s), 0.88 (3H, s). (Found: C, 59.35; H, 6.05. $C_{27}H_{32}F_2O_7S$. 0.4 $H_2O$ requires C, 59.42; H, 6.06%).

Example 13

6α,9α-Difluoro-11β-hydroxy-16α,17α-isopropylidenedioxy-3-oxo-androsta-1,4-diene-17β-carbothioic acid S-(2-oxo-tetrahydro-furan-5-yl) ester.

Powdered anhydrous potassium carbonate (61 mg, 0.44 mmol) was added to a stirred solution of 6α,9α-difluoro-11β-hydroxy-16α,17α-isopropylidenedioxy-3-oxo-androsta-1,4-diene-17β-carbothioic acid (200 mg, 0.44 mmol) in dry DMF (5 ml). The mixture was stirred under nitrogen and then cooled in ice. γ-Chloro-γ-butyrolactone (64 mg, 0.53 mmol) in dry DMF (1 ml) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by flash column chromatography on silica gel, eluting with cyclohexane-ethyl acetate (1:1) to give the title compound isomer-A as a crystalline solid (67 mg, 28%): mp. 304–307° C.; MS (TSP+ve) m/z 539 [MH]$^+$; IR $\nu_{max}$ (KBr) 1784, 1697, 1668, 1630 cm$^{-1}$; NMR δ (CDCl$_3$) includes 7.14 (1H, d, J 10 Hz), 6.42 (1H, s), 6.39 (1H, d, J 10 Hz), 6.31 (1H, m), 5.50 and 5.30 (1H, 2m), 5.00 (1H, m), 4.42 (1H, m), 1.65 (3H, s), 1.49 (3H, s), 1.37 (3H, s), 1.00 (3H, s). (Found: C, 59.76; H, 6.13; S, 5.80. $C_{27}H_{32}F_2O_7S$.0.2 $H_2O$ requires C, 59.81; H, 6.02; S, 5.91%) and the title compound isomer B as a crystalline solid (67 mg, 28%): mp. 270–273° C.; MS (TSP+ve) m/z 539 [MH]$^+$; IR $\nu_{max}$ (KBr) 1792, 1700, 1666, 1629 cm$^{-1}$; NMR δ (DMSO d$_6$) includes 7.26 (1H, d, J 10 Hz), 6.31 (1H, d, J 10 Hz), 6.15(2H, m), 5.74 and 5.54 (1H, 2m), 5.56 (1H, s), 4.93 (1H, m), 4.20 (1H, m), 1.50 (3H, s), 1.35 (3H, s), 1.14 (3H, s), 0.90 (3H, s). (Found: C, 59.16; H, 6.01; S, 5.54. $C_{27}H_{32}F_2O_7S$.0.5 $H_2O$ requires C, 59.22; H, 6.07; S, 5.86%).

Example 14

6α,9α-Difluoro-11β-hydroxy-16α,17α-isopropylidenedioxy-3-oxo-androst-4-ene-17β-carbothioic acid S-(2-oxo-tetrahydro-furan-3-yl) ester.

To a stirred suspension of 6α,9α-difluoro-11β-hydroxy-16α,17α-isopropylidenedioxy-3-oxo-androst-4-ene-17β-carbothioic acid (448 mg, 1.02 mmol) in dichloromethane (8 ml) was added triethylamine (160 μl, 1.15 mmol) followed by diethylchlorophosphate (160 μl, 1.11 mmol) and the mixture stirred to allow formation of the intermediate mixed anhydride. A solution of the sodium salt of α-mercapto-γ-butyrolactone [made by addition of sodium hydride (70 mg of 60% oil dispersion, 1.75 mmol) to a solution of α-mercapto-γ-butyrolactone (170 mg, 1.44 mmol) in DMF (4 ml)] was added and the reaction followed by TLC analysis. On completion the reaction was diluted with ethyl acetate (50 ml) and washed with 1M HCl (2×50 ml), water (50 ml), saturated sodium bicarbonate solution (2×50 ml), water (50 ml) and saturated brine solution (50 ml). The organic layer was then dried and concentrated to yield the crude material as a gum. This was purified by flash column chromatography on silica gel, eluting with ethyl acetate-cyclohexane (1:1). The title compound isomer A was isolated as a crystalline solid (60 mg, 11%): mp. 169–173° C.; MS (TSP+ve) m/z 541 [MH]$^+$; IR $\nu_{max}$ (KBr) 3397, 2959, 1780, 1690, 1657 cm$^{-1}$; NMR δ (CDCl$_3$) includes 6.17 (1H, s), 5.36 and 5.24 (1H, 2m), 5.05 (1H, d, J 5 Hz), 4.49 (1H, t, J 4 Hz), 4.44–4.34 (3H, m), 1.55 (3H, s), 1.51 (3H, s), 1.29 (3H, s), 1.03 (3H, s). (Found: C, 58.92; H, 6.03; S, 6.25. $C_{27}H_{34}F_2O_7S$ 0.4 $H_2O$ requires C, 59.20; H, 6.40; S, 5.85%) and the title compound isomer B isolated as a foam (79 mg, 14%): MS (TSP+ve) m/z 541 [MH]$^+$; IR $\nu_{max}$ (KBr) 3379, 1780, 1691, 1658 cm$^{-1}$; NMR δ (CDCl$_3$) includes 6.17 (1H, s), 5.36 and 5.24 (1H, 2m), 5.02 (1H, d, J 5 Hz) 4.59 (1H, t, J 4.5 Hz), 4.46–4.25 (2H, m), 3.98 (1H, t, J 10 Hz), 1 54 (3H, s), 1.51 (3H, s), 1.32 (3H, s), 0.98 (3H, s). (Found: C, 59.32; H 6.43; S, 5.96. $C_{27}H_{34}F_2O_7S$.0.3 $H_2O$ requires C, 59.39; H, 6.39; S, 5.87%).

Example 15

6α,9α-Difluoro-11β-hydroxy-16α,17α-isopropylidenedioxy-3-oxo-androsta-1,4-diene-17β-carboxylic acid N-(2-oxo-tetrahydro-furan-3S-yl) amide A mixture of 6α,9α-difluoro-11β-hydroxy-16α,17α-isopropylidenedioxy-3-oxo-androsta-1,4-diene-17β-carboxylic acid (100 mg, 0.228 mmol), (S)-α-amino-γ-butyrolactone hydrochloride (46 mg, 0.202 mmol), 1-hydroxy-benzotriazole (31 mg, 0.228 mmol), O-(1H-benzotriazol-1-yl)-N,N,N'N'-tetramethyluronium tetrafluoroborate (81 mg, 0.251 mmol) and diisopropylethylamine (0.04 ml, 0.228 mmol) in DMF (5 ml) was stirred and heated at 100° C. under an atmosphere of nitrogen until the reaction was complete, as monitered by TLC analysis. After cooling to room temperature ethyl acetate (20 ml) and hydrochloric acid (2M, 15 ml) were added. The aqueous layer was separated and extracted with ethyl acetate (20 ml). The combined organic layers were washed with water (15 ml) and saturated brine solution (15 ml), dried over anhydrous MgSO$_4$ and concentrated to yield the crude product as a gum. This was purified by flash column chromatography on silica gel, eluting with ethyl acetate, to yield the title compound as a crystalline solid (60 mg, 57%): mp. 181–184° C.; MS (TSP+ve) 522 [MH]$^+$; IR $\nu_{max}$ (KBr) 3320, 1774, 1669, 1633 cm$^{-1}$; NMR δ (CDCl$_3$) includes 7.18 (1H, d, J 10 Hz), 6.93 (1H, bs), 6.42 (1H, s), 6.38 (1H, d, J 10 Hz), 5.50 and 5.30 (1H, 2m), 5.08 (1H, bs), 4.91 (1H, m), 4.51 (1H, m), 4.33 (2H, m), 2.72 (1H, m), 1.79 (3H, s), 1.35 (3H, s), 1.22 (3H, s), 1.04 (3H, s). (Found: C, 60.63; H, 6.59; N, 2.44. $C_{27}H_{33}F_2NO_7 \cdot 0.7\ H_2O$ requires C, 60.71; H, 6.49; N, 2.62%).

Example 16

6α,9α-Difluoro-11β-hydroxy-16α,17α-isopropylidenedioxy-3-oxo-androsta-1,4-diene-17β-carboxylic acid N-(2-oxo-tetrahydro-furan-3-yl) amide A mixture of 6α,9α-difluoro-11β-hydroxy-16α,17α-isopropylidenedioxy-3-oxo-androsta-1,4-diene-17β-carboxylic acid (259 mg, 0.591 mmol), (±)-α-amino-γ-butyrolactone hydrochloride (108 mg, 0.591 mmol), 1-hydroxy-benzotriazole (80 mg, 0.591 mmol), 1-(3-dimethylamino-propyl)-3-ethyl-carbodiimide hydrochloride (113 mg, 0.591 mmol) and diisopropylethylamine (0.11 ml, 0.650 mmol) in dimethylformamide (20 ml) was stirred and heated at 100° C. under an atmosphere of nitrogen until the reaction was complete, as monitered by TLC analysis. After cooling to room temperature ethyl acetate (20 ml) and hydrochloric acid (2M, 5 ml) were added. The aqueous layer was separated and extracted with ethyl acetate (20 ml). The combined organic layers were washed with water (15 ml) and saturated brine solution (15 ml), dried over anhydrous $MgSO_4$ and concentrated to yield the crude product as a gum. This was purified by preparative layer chromatography on silica gel, eluting with 5:2 ethyl acetate:cyclohexane, to yield the title compound S-isomer, isomer A, as a crystalline solid as obtained above and the title compound R-isomer, isomer B, as a crystalline solid (40 mg, 13%). mp. 333–336° C.; MS (TSP+ve) 522 [MH]$^+$; IR $v_{max}$ (KBr) 3484, 1775, 1668, 1632 cm$^{-1}$; NMR δ (DMSO d$_6$) includes 8.32 (1H, s), 7.24 (1H, d, J 10 Hz), 6.30 (1H, d, J 10 Hz), 6.10 (1H, s), 5.72 and 5.52 (1H, 2m), 5.52 (1H, bs), 4.95 (1H, m), 4.57 (1H, m), 4.34 (1H, m), 4.20 (1H, m), 2.00 (3H, s), 1.34, (3H, s) 1.17 (3H, s), 0.91 (3H, s). (Found: C, 62.51; H, 6.61; N, 2.33%, $C_{27}H_{33}F_2NO_7$ requires C, 62.18; H, 6.38; N, 2.69%).

Example 17

6α,9α-Difluoro-11β-hydroxy-16α,17α-isopropylidenedioxy-3-oxo-androsta-1,4-diene-17β-carboxylic acid (2-oxo-tetrahydro-furan-3-yl) ester.

Powdered anhydrous potassium carbonate (65 mg, 0.47 mmol) was added to a stirred solution of 6α,9α-difluoro-11β-hydroxy-16α,17α-isopropylidenedioxy-3-oxo-androsta-1,4-diene-17β-carboxylic acid (205 mg, 0.47 mmol) in dry DMF (4 ml). The mixture was stirred under nitrogen and then cooled in ice. α-Bromo-γ-butyrolactone (50 μl, 0.58 mmol) was then added and the mixture stirred until reaction was complete as monitored by TLC. The solution was partitioned between water (25 ml) and ethyl acetate (25 ml). The organic phase was separated, washed with water (2×25 ml) dried and evaporated to a solid. The crude product was purified by preparative layer chromatography on silica gel, eluting with chloroform-cyclohexane-ethanol (10:10:1), to give the title compound isomer A as a crystalline solid (65 mg, 27%): mp. 253–255° C.; MS (TSP+ve) m/z 523 [MH]$^+$; IR $v_{max}$ (KBr) 1785, 1732, 1667, 1631 cm$^{-1}$; NMR δ (DMSO d$_6$) includes 7.20 (1H, d, J 10 Hz), 6.44 (1H, s), 6.39 (1H, d, J 10 Hz), 5.68 (1H, m), 5.49 and 5.30 (1H, 2m), 5.18(1H, m), 4.52 (1H, m), 4.37(2H, m), 2.71 (1H, m), 1.52 (3H, s), 1.42 (3H, s), 1.21 (3H, s), 1.08 (3H, s). (Found: C, 61.43; H, 6.07. $C_{27}H_{32}F_2O_8$ 0.3 $H_2O$ requires C, 61.43; H, 6.22%) and the title compound isomer B as a crystalline solid (53.2 mg, 22%): mp. 300–304° C.; MS (TSP+ve) m/z 523 [MH]$^+$: IR $v_{max}$ (KBr) 1793, 1743, 1666, 1632 cm$^{-1}$; NMR δ (DMSO d$_6$) includes 7.10 (1H, d, J 10 Hz), 6.44 (1H, s), 6.39 (1H, d, J 10 Hz), 5.49 and 5.30 (1H, 2m), 5.38 (1H, m), 5.15 (1H, m), 4.46 (1H, m), 4.39 (2H, m), 2.70 (1H, m), 1.52 (3H, s), 1.42 (3H, s), 1.25 (3H, s), 1.06 (3H, s). (Found: C, 61.76; H, 6.11. $C_{28}H_{32}F_2O_8$ requires C, 62.06; H, 6.17%).

Example 18

6α,17α-Butylidenedioxy-11β-hydroxy-3-oxo-androsta-1,4-diene-17β-carbothioic acid S-(2-oxo-tetrahydro-turan-3-yl) ester.

Powdered anhydrous potassium carbonate (24 mg, 0.175 mmol) was added to a stirred solution of 16α,17α-butylidenedioxy-11β-hydroxy-3-oxo-androsta-1,4-diene-17β-carbothioic acid (69 mg, 0.16 mmol) in dry DMF (1.5 ml). The mixture was stirred under nitrogen and then cooled in ice. α-Bromo-γ-butyrolactone (16.5 μl, 0.20 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative normal phase HPLC (Dynamax 60 Å C18, 25 cm×41 mm i.d.) eluting with 70–90% ethyl acetate/heptane at 45 ml/min with detection at 270 nm and the title compound diastereomeric mixture A isolated as a crystalline solid (23 mg, 28%): mp. 129–132° C.; MS (TSP+ve) m/z 517 [MH]$^+$; IR vrax (KBr) 3459, 1775, 1693, 1653, 1618 cm$^{-1}$; NMR δ (DMSO d$_6$) includes 7.30 (1H, d, J 10 Hz), 6.18 (1H, d, J 10 Hz), 5.91 (1H, s), 4.87 (1H, m), 4.65 (2H, m), 4.30 (4H, m), 1.38 (3H, s), 0.97 (6H, m). (Found: C, 64.34; H, 7.24; S, 5.39. $C_{28}H_{36}O_7S$ 0.5 $H_2O$ requires C, 64.26; H, 7.19; S, 5.72%) and the title compound diastereomeric mixture B as a crystalline solid (29 mg, 35%) mp. 149–154° C.; MS (TSP+ve) m/z 539 [MH]$^+$; IR $v_{max}$ (KBr) 3468, 1775, 1688, 1654, 1617 cm$^{-1}$; NMR δ (DMSO d$_6$) includes 7.30 (1H, d, J 10 Hz), 6.16 (1H, d, J 10 Hz), 5.90 (1H, s), 4.86 (1H, m), 4.68 (2H, m), 4.30 (4H, m), 1.37 (3H, s), 0.90 (6H, m) (Found: C, 64.43; H, 7.12; S, 5.78. $C_{28}H_{36}O_7S \cdot 0.3\ H_2O$ requires C, 64.42; H, 7.07; S, 6.14%).

Example 19

16α,17α-(R-Butylidenedioxy)-6α,9α-difluoro-11β-hydroxy-3-oxo-androst-4-ene-17β-carbothioic acid S-(2-oxo-tetrahydro-furan-3-yl) ester.

To a stirred suspension of 16α,17α-(R-butylidenedioxy)-6α,9α-difluoro-11β-hydroxy-3-oxo-androst-4-ene-17β-carboxylic acid (200 mg, 0.44 mmol) in dichloromethane (3 ml) was added triethylamine (61 μl, 0.44 mmol) followed by diethylchlorophosphate (64 μl, 0.44 mmol) and the mixture stirred to allow formation of the intermediate mixed anhydride. A solution of the sodium salt of α-mercapto-γ-butyrolactone [made by addition of sodium hydride (24 mg of 60% oil dispersion, 0.6 mmol) to a solution of α-mercapto-γ-butyrolactone (72 mg, 0.6 mmol) in DMF (1.5 ml)] was added and the reaction followed by TLC analysis. On completion the reaction was diluted with ethyl acetate (50 ml) and washed with 1M hydrochloric acid (2×50 ml), water (50 ml), saturated sodium bicarbonate solution (2×50 ml), water (50 ml) and saturated brine solution (50 ml). The organic layer was then dried and concentrated to yield the crude material as a gum. This was purified by preparative layer chromatography on silica gel, eluting ethyl acetate-40–60 petroleum ether (1:1). The title compound isomer A was isolated as a foam after trituration with diethyl ether (84.5 mg, 35%): MS (TSP+ve) m/z 555 [MH]$^+$; IR $v_{max}$ (KBr) 3480, 1777 cm$^{-1}$; NMR δ (CDCl$_3$) includes 6.15 (1H, s), 5.37 and 5.18 (1H, 2m), 4.85 (1H, d, J 5 Hz), 4.74 (1H, t, J 4 Hz), 4.40 (1H, m), 4.54–4.22 (3H, m), 1.53 (3H, s), 1.02 (3H, s), 0.96 (3H, t, J 7.5 Hz). Found: C, 60.91; H, 7.05; S, 5.48. $C_{28}H_{36}F_2O_7S$ 0.55 Et$_2$O requires C, 60.92; H, 7.03; S, 5.39%) and the title compound isomer B isolated as a foam (68 mg, 31%): MS (TSP+ve) m/z 555 [MH]⁺; IR $v_{max}$ (KBr) 3466, 1771 cm⁻¹; NMR δ (CDCl₃) includes 6.14 (1H, s), 5.36 and 5.18 (1H, 2m), 4.82 (1H, d, J 5 Hz), 4.77 (1H, t, J 4.5 Hz), 4.35 (4H, m), 1.52 (3H, s), 0.96 (6H, t, s, J 7.5 Hz). (Found: C, 61.22; H, 7.06; S, 5.39. $C_{28}H_{36}F_2O_7S$ 0.2 $C_5H_{12}$ requires C, 61.37; H, 6.68; S, 5.59%).

Example 20

16α,17α-(R-Butylidenedioxy)-6α,9α-difluoro-11β-hydroxy-3-oxo-androsta-1,4-diene-17β-carbothioic acid S-(2-oxo-tetrahydro-furan-3-yl) ester.

To a suspension of sand (10 g) in heptane (12.5 ml) at room temperature was added 6α,9α-difluoro-11β-hydroxy-16α,17α-isopropylidenedioxy-3-oxo-androsta-1,4-diene-17β-carbothioic acid S-(2-oxo-tetrahydro-furan-3-yl) ester (Example 12, 0.5 g, 0.93 mmol) with vigorous stirring. To this suspension was added butanal (0.123 ml, 1.39 mmol) followed by perchloric acid (0.320 ml, 3.71 mmol) and the suspension stirred at room temperature until reaction was complete as evidenced by TLC analysis. The reaction was cooled in ice before addition of 10% aq. $K_2CO_3$ solution (8 ml), ensuring the internal temperature did not rise above 25° C. The sand was collected by filtration and washed with heptane (4×20 ml), water (6×20 ml) then ethyl acetate (4×40 ml) and the combined ethyl acetate layers washed with brine solution (20 ml) and dried before concentrating to yield the crude product as a solid. The material was purified by flash column chromatography on silica gel, eluting with ethyl acetate-cyclohexane (3:2). The title compound isomer A was isolated as a crystalline solid (74 mg, 15%): mp. 260–264° C.; MS (TSP+ve) m/z 553 [MH]⁻¹; IR $v_{max}$ (KBr) 3341, 1774, 1698, 1668, 1629 cm⁻¹; NMR δ (DMSO $d_6$) includes 7.25 (1H, d, J 10 Hz), 6.30 (1H, d, J 10 Hz), 6.10 (1H, bs), 5.70 and 5.55 (1H, 2m), 5.60 (1H, bs), 4.70 (2H, m), 4.50–4.15 (4H, m), 1.48 (3H, s), 0.95 (3H, s), 0.86 (3H, t, J 7 Hz). (Found: C, 60.72; H, 6.01; S, 5.51. $C_{28}H_{34}F_2O_7S$ requires C, 60.86; H, 6.20; S, 5.80%) and the title compound isomer B, also as a crystalline solid (53 mg, 10%): mp. 254–257° C.; MS (TSP+ve) m/z 553 [MH]⁺; IR $v_{max}$ (KBr) 3376, 1776, 1693, 1667, 1623 cm⁻¹; NMR δ (DMSO $d_6$) includes 7.25 (1H, d, J 10 Hz), 6.25 (1H, d, J 10 Hz), 6.10 (1H, bs), 5.70 and 5.55 (1H, 2m), 5.60 (1H, bs), 4.70 (1H, m), 4.50–4.15 (4H, m), 1.47 (3H, s), 0.86 (6H, m). (Found: C, 60.91; H, 6.09; S, 5.62. $C_{28}H_{34}F_2O_7S$ requires C, 60.86; H, 6.20; S, 5.80%).

Example 21

16α,17α-Butylidenedioxy-11β-hydroxy-3-oxo-andrqrta-1,4-diene-17-carboxylic acid (2-oxo-tetrahydro-furan-3-yl) ester.

Powdered anhydrous potassium carbonate (37 mg, 0.264 mmol) was added to a stirred solution of 16α,17α-butylidenedioxy-6α,9α-difluoro-11β-hydroxy-3-oxo-androsta-1,4-diene-17β-carboxyiic acid (100 mg, 0.24 mmol) in dry DMF (1.3 ml). The mixture was stirred under nitrogen and then cooled in ice. α-Bromo-γ-butyrolactone (25 μl, 0.30 mmol) was then added and the mixture stirred until reaction was complete as monitored by TLC. The solution was partitioned between water (25 ml) and ethyl acetate (25 ml). The organic phase was separated, washed with water (2×25 ml), dried and evaporated to a solid. The crude product was purified by preparative reversed phase HPLC (Dynamax 60 Å C18, 25 cm×41 mm i.d.) eluting with 70–90% MeCN/H₂O at 45 ml/min with detection at 230 nm and the title compound diastereomeric mixture A isolated as a crystalline solid (41 mg, 34%): mp. 177–180° C.; MS (TSP+ve) m/z 501 [MH]⁺; IR $v_{max}$ (KBr) 3515, 1789, 1738, 1653, 1616 cm⁻¹; NMR δ (DMSO $d_6$) includes 7.30 (1H, d, J 10 Hz), 6.18 (1H, d, J 10 Hz), 5.91 (1H, s), 5.65 (1H, m), 5.18 (1H, m), 4.86 (2H, m), 4.38 (3H, m), 1.38 (3H, s), 0.93 (3H, s), 0.85 (3H, t, J 7 Hz). (Found: C, 66.31; H, 7.30. $C_{28}H_{36}O_8$. 0.4 H₂O requires C, 66.23; H, 7.30%) and the tile compound diastereomeric mixture B as a crystalline solid (38 mg, 31%): mp. 128–133° C.; MS (TSP+ve) m/z 501 [MH]⁺; IR $v_{max}$ (KBr) 3490, 1789, 1738, 1653, 1614 cm⁻¹; NMR δ (DMSO $d_6$) includes 7.30 (1H, d, J 10 Hz), 6.17 (1H, d, J 10 Hz), 5.92 (1H, s), 5.60 (1H, m), 4.77 (3H, m), 4.32 (3H, m), 1.38 (3H, s), 0.95 (3H, s), 0.84 (3H, t, J 7 Hz). (Found: C, 65.73; H, 7.23. $C_{28}H_{36}O_8$.0.6 H₂O requires C, 65.76; H, 7.33%).

Example 22

16α,17α-(R-Butylidenedioxy)-6α,9α-difluoro-11β-hydroxy-3-oxo-androst-4-ene-17β-carboxylic acid N-(2-oxo-tetrahydro-furan-3-yl) amide A mixture of 16α,17α-(R-butylidenedioxy)-6α,9α-difluoro-11β-hydroxy-3-oxo-androst-4-ene-17β-carboxylic acid (0.98 g, 2.16 mmol), (±)-α-amino-γ-butyrolactone hydrobromide (393 mg, 2.16 mmol), 1-hydroxy-benzotriazole (292 mg, 2.16 mmol), O-(1H-benzotriazol-1-yl)-N,N,N'N'-tetramethyluronium tetrafluoroborate (692 mg, 2.16 mmol) and diisopropylethylamine (1.13 ml, 6.48 mmol) in DMF (25 ml) was stirred and heated at 100° C. under an atmosphere of nitrogen until the reaction was complete, as monitored by TLC analysis. After cooling to room temperature ethyl acetate (100 ml) and 2M hydrochloric acid (100 ml) were added. The organic layer was separated and extracted successively with water (100 ml), 1M aqueous sodium hydroxide solution (100 ml), water (100 ml) and saturated brine solution (100 ml). The organic layer was dried over anhydrous MgSO₄ and concentrated to yield the crude product as a gum. This was purified by flash column chromatography on silica gel, eluting with ethyl acetate:cyclohexane (1:1) followed by ethyl acetate, to yield two fractions. These were further purified by reverse phase preparative HPLC (Dynamax 60A C18, 25 cm×41 mm i.d.) eluting with 47% MeCN/H₂O at 45 mlmin with detection at 230 nm, in both cases. The less polar fraction afforded the title compound isomer A as a white solid (30 mg, 3%): mp. 165° C.; MS (TSP+ve) 538 [MH]⁻; IR $v_{max}$ (KBr) 3468, 3407, 3351,1778,1663, 1520 cm⁻¹; NMR δ (CDCl₃) includes 6.72 (1H, d, J 8 Hz), 6.14 (1H, s), 5.38 and 5.18 (1H, 2m), 4.98 (1H, d, J 5 Hz), 4.82 (1H, m), 4.67 (1H, t, J 4 Hz), 4.50 (1H, t, J 9 Hz), 4.37 (2H, m), 1.05 (3H, s), 0.95 (3H, t, J 7 Hz). (Found: C, 63.00; H, 6.75; N, 2.13. $C_{28}H_{37}F_2NO_7$ requires C, 62.51; H, 6.88; N, 2.60%). The more polar fraction was further purified by preparative TLC, eluting several times with ethyl acetate:cyclohexane (3:1), to afford the title compound isomer B as a white solid (25 mg, 2%): mp. 155–160° C.; MS (TSP+ve) 538 [MH]⁺; IR $v_{max}$ (KBr) 3382, 1779, 1668, 1516 cm⁻¹; NMR δ (CDCl₃) includes 6.98 (1H, d, J 6 Hz), 6.13 (1H, s), 5.37 and 5.18 (1H, 2m), 4.94 (1H, d, J 5 Hz), 4.54 (1H, t, J 4 Hz), 4.53 (1H, t, J 9 Hz), 4.484.24 (3H, m), 1.02 (3H, s), 0.94 (3H, t, J 7 Hz). (Found: C, 60.94; H, 7.15; N, 2.21. $C_{28}H_{37}F_2NO_7$ 0.8 H₂O requires C, 60.92; H, 7.05; N, 2.54%).

Example 23

6α,9α-Difluoro-11β-hydroxy-16α,17α-isopropylidenedioxy-3-oxo-androsta-1,4-diene-17β-carboxylic acid N-(2-oxo-tetrahydro-furan-4S-yl) amide A mixture of 6α,9α-difluoro-11β-hydroxy-16α,17α-isopropylidenedioxy-3-oxo-androsta-1,4-diene-17β-carboxylic acid (0.5 g, 1.14 mmol), 4S-amino-γ-butyrolactone hydrobromide (207 mg, 1.14 mmol), 1-hydroxy-benzotriazole (154 mg, 1.14 mmol), O-(1H- benzotriazol-1-yl)-N,N,N'N'-tetramethyluronium tetrafluoroborate (365 mg, 1.14 mmol) and diisopropylethylamine (0.6 ml, 3.44 mmol) in DMF (15 ml) was stirred and heated at 100° C. under an atmosphere of nitrogen until the reaction was complete, as monitored by TLC analysis. After cooling to room temperature ethyl acetate (100 ml) and 2M hydrochloric acid (100 ml) were added. The organic layer was separated and extracted successively with 1M aqueous sodium hydroxide solution (100 ml) and saturated brine solution (100 ml). The organic layer was dried over anhydrous $MgSO_4$ and concentrated to yield the crude product as a gum. This was purified by reverse phase preparative HPLC (Dynamax 60A C18, 25 cm×41 mm i.d.) eluting with 40% $MeCN/H_2O$ at 45 ml/min with detection at 230 nm affording the title compound as a white solid (129 mg, 22%): mp. 204–206° C.; MS (TSP+ve) 522 [MH]$^+$; IR $v_{max}$ (KBr) 3325, 1778, 1667,1631, 1527 cm$^{-1}$; NMR δ (DMSO d$_6$) includes 8.44 (1H, d, J 6 Hz), 7.26 (1H, d, J 10 Hz), 6.30 (1H, d, J 10 Hz), 6.11 (1H, s), 5.74 and 5.55 (1H, 2m), 5.46 (1H, s), 4.95 (1H, d, J 2 Hz), 4.57 (1H, m), 4.48 (1H, dd, J 8 and 8 Hz), 4.17 (1H, bd), 4.08 (1H, dd, J 9 and 2 Hz), 2.83 (1H, dd, J 17 and 8 Hz), 1.51 (3H, s), 1.34 (3H, s), 1.12 (3H, s), 0.88 (3H, s). (Found: C, 61.17; H, 6.55; N, 3.35. $C_{27}H_{33}F_2NO_7$.0.3 $CH_3CN$ .0.4 $H_2O$ requires C, 61.27; H, 6.46; N, 3.37%).

Example 24

6α,9α-Difluoro-11β-hydroxy-16α,17α-isopropylidenedioxy-3-oxo-androsta-1,4-diene-17β-carboxylic acid N-(2-oxo-tetrahydro-furan-4R-yl) amide A mixture of 6α,9α-difluoro-11β-hydroxy-16α,17α-isopropylenedioxy-3-oxo-androsta-1,4-diene-17β-carboxylic acid (0.5 g, 1.14 mmol), 4R-amino-γ-butyroiactone hydrobromide (207 mg, 1.14 mmol), 1-hydroxy-benzotriazole (154 mg, 1.14 mmol), O-(1H-benzotriazol-1-yl)-N,N,N'N'-tetramethyluronium tetrafluoroborate (365 mg, 1.14 mmol) and diisopropylethylamine (0.6 ml, 3.44 mmol) in DMF (15 ml) was stirred and heated at 100° C. under an atmosphere of nitrogen until the reaction was complete, as monitored by TLC analysis. After cooling to room temperature ethyl acetate (100 ml) and 2M hydrochloric acid (100 ml) were added. The organic layer was separated and extracted successively with 1M aqueous sodium hydroxide solution (100 ml) and saturated brine solution (100 ml). The organic layer was dried over anhydrous $MgSO_4$ and concentrated to yield the crude product as a gum. This was purified by flash column chromatography on silica gel, eluting with ethyl acetate:cyclohexane (4:1) and was further purified by reverse phase preparative HPLC (Dynamax 60A C18, 25 cm×41 mm i.d.) eluting with 40% $MeCN/H_2O$ at 45 ml/min with detection at 230 nm affording the title compound as a white solid (99 mg, 17%): mp. 322° C.; MS (TSP+ve) 522 [MH]$^+$; IR $v_{max}$ (KBr) 3360, 1780, 1768, 1666, 1627, 1534 cm$^{-1}$; NMR δ (DMSO d$_6$) includes 8.50 (1H, d, J 7 Hz), 7.26 (1H, d, J 10 Hz), 6.30 (1H, dd, J 10 and 1 Hz), 6.11 (1H, s), 5.73 and 5.54 (1H, 2m), 5.43 (1H, bd, J 1 Hz), 4.95 (1H, d, J 4 Hz), 4.58 (1H, m), 4.43 (1H, dd, J 8 and 8 Hz), 4.37 (1H, bd), 4.03 (1H, dd, J 9 and 4 Hz), 2.83 (1H, dd, J 18 and 9 Hz), 1.50 (3H, s), 1.34 (3H, s), 1.13 (3H, s), 0.88 (3H, s). (Found: C, 61.46; H, 6.48; N, 2.76. $C_{27}H_{33}F_2NO_7$.0.3 $H_2O$ requires C, 61.54; H, 6.43; N, 2.66%).

Example 25

6α,9α-Difluoro-11β-hydroxy-16α,17α-isopropylidenedioxy-3-oxo-androsta-1,4-diene-17β-carbothioic acid S-(2-oxo-tetrahydrofuran-3S-yl) ester.

Powdered anhydrous potassium carbonate (34 mg, 0.32 mmol) was added to a stirred solution of 6α,9α-difluoro-11β-hydroxy-16α,17α-isopropylidenedioxy-3-oxo-androsta-1,4-diene-17β-carbothioic acid (250 mg, 0.55 mmol) in dry DMF (10 ml). The mixture was stirred under nitrogen for fifteen minutes. Methanesulfonic acid 2-oxo-tetrahydro-furan-3R-yl ester (Intermediate 4, 99 mg, 0.55 mmol) was then added and the mixture stirred for ten minutes. The solution was partitioned between saturated sodium bicarbonate solution (50 ml) and ethyl acetate (50 ml), washed with 2M hydrochloric acid solution (50 ml), dried and evaporated to a solid. The crude product was purified by flash chromatography on silica gel, eluting with ethyl acetate-cyclohexane (1:1) followed by ethyl acetate-cyclohexane (3:1) to afford the title compound as a white solid (148 mg, 50%): mp. 310–314° C.; MS (ES+ve) m/z 539 [MH]$^+$; NMR δ (CDCl$_3$) includes 7.14 (1H, dd, J 10 and 1 Hz), 6.44 (1H, s), 6.38 (1H, dd, J 10 and 1 Hz), 5.49 and 5.29 (1H, 2m), 5.01 (1H, d, J 4 Hz), 4.58–4.30 (4H, m), 1.53 (3H, s), 1.44 (3H, s), 1.25 (3H,s), 1.02 (3H, s). This compound is identical with isomer A of Example 12.

Example 26

6α,9α-Difluoro-11β-hydroxy-16α,17α-isopropylidenedioxy-3-oxo-androsta-1,4-diene-17β-carbothioic acid S-(2-oxo-tetrahydro-furan-3R-yl) ester.

Powdered anhydrous potassium carbonate (34 mg, 0.32 mmol) was added to a stirred solution of 6α,9α-difluoro-11β-hydroxy-16α,17α-isopropylidenedioxy-3-oxo-androsta-1,4-diene-17β-carbothioic acid (250 mg, 0.55 mmol) in dry DMF (10 ml). The mixture was stirred under nitrogen for thirty minutes. Methanesulfonic acid 2-oxo-tetrahydro-furan-3S-yl ester (Intermediate 5, 99 mg, 0.55 mmol) was then added and the mixture stirred for fifteen minutes. The solution was partitioned between saturated sodium bicarbonate solution (50 ml) and ethyl acetate (50 ml), washed with 2M hydrochloric acid solution (50 ml), dried and evaporated to a solid. The crude product was purified by flash chromatography on silica gel, eluting with ethyl acetate-cyclohexane (1:1) followed by ethyl acetate-cyclohexane (3:1) to afford the title compound as a white solid (120 mg, 41%): mp. 284–287° C.; MS (ES+ve) m/z 539 [MH]$^+$; NMR δ (CDCl$_3$) includes 7.13 (1H, dd, J 10 and 1 Hz), 6.43 (1H, s), 6.38 (1H, dd, J 10 and 1 Hz), 5.48 and 5.28 (1H, 2m), 4.97 (1H, d, J 4 Hz), 4.60 (1H, J 9 and 3 Hz), 4.45–4.3 (2H, m), 3.91 (1H, t, J 10 Hz), 1.53 (3H, s), 1.45 (3H, s), 1.27 (3H,s), 0.96 (3H, s). This compound is identical to isomer B of Example 12.

Example 27

16α,17α-(R-Butylidenedioxy)-6α,9α-difluoro-11β-hydroxy-3-oxo-androst-4-ene-17β-carbothioic acid (5-oxo-tetrahydro-furan-2-yl) ester.

Powdered anhydrous potassium carbonate (29 mg, 0.21 mmol) was added to a stirred solution of 16α,17α-(R-butylidenedioxy)-6α,9α-difluoro-11β-hydroxy-3-oxo-androst-4-ene-17β-carbothioic acid (Intermediate 7, 100 mg, 0.21 mmol) in dry DMF (2 ml). The mixture was stirred under nitrogen, γ-chloro-γ-butyrolactone (42 mg, 0.35 mmol) was added and the mixture stirred until reaction was complete as monitored by TLC. The solution was partitioned between water (25 ml) and ethyl acetate (25 ml). The organic phase was separated, washed with water (2×25 ml), dried and evaporated to a gum. The crude product was purified by preparative layer chromatography on silica gel, eluting with diethyl ether to give the title compound as a foam (24 mg, 21%): MS (ES+ve) m/z 555 [MH]$^+$; IR $v_{max}$ (KBr) 3484, 1790, 1700, 1665 cm$^{-1}$; NMR δ (CDCl$_3$) includes 6.24 (0.5H, dd, J 8 and 6 Hz), 6.15 and 6.14 (1H, 2s), 5.86 (0.5H, dd J 5 and 1 Hz), 5.33 and 5.21 (1 H, 2m), 4.84 (0.5H, d, J 5.5 Hz), 4.80 (0.5H, t, J 4.5 Hz), 4.78 (0.5H, d, J 5.5 Hz), 4.71 (0.5H, t, J 4.5 Hz), 4.44 and 4.38 (1H, 2m), 1.53 and 1.52 (3H, 2s), 1.00–0.92 (6H, m). The individual diastereoisomers were separated by further preparative layer chromatography on silica gel, eluting with diethyl ether (×3) to give the title compound isomer A as a foam (8 mg, 7%): MS (ES+ve) m/z 555 [MH]$^+$; NMR δ (CDCl$_3$) includes 6.24 (1H, t, J 7 Hz), 6.14 (1H, s), 5.38 and 5.28 (1H, 2m), 4.84 (1H, d, J 5 Hz), 4.71 (1H, t, J 4.5 Hz), 4.38 (1H, m), 1.52 (3H, s), 0.97 (6H, m), and the title compound isomer B as a foam (5 mg, 4%): IR $\nu_{max}$ (KBr) 3448, 1790, 1713, 1681, 1651 cm$^{-1}$; NMR δ (CDCl$_3$) includes 6.15 (1H, s), 5.87 (1H, dd, J 4 and 1 Hz), 5.38 and 5.18 (1H, 2m), 4.79 (2H, m), 4.44 (1H, m), 1.53 (3H, s), 0.98 (6H, m).

Pharmacological Activity

In Vitro

The pharmacological activity was studied in a functional in vitro assay to demonstrate glucocorticoid activity which is generally predictive of anti-inflammatory or anti-allergic activity in-vivo.

The functional assay used was a modification of the method described by T. S Berger et al, of J. of Steroid Biochem. Molec. Biol. 1992, 41 (3–8), 733–738, "Interaction of Glucocorticoid analogues with the Human Glucocorticoid Receptor".

Thus, Hela cells were stably transfected with a detectable reporter gene (secreted placental alkaline phosphatase, sPAP) under the control of a glucocorticoid response promoter (the LTR of the mouse mammary tumour virus, MMTV).

Various concentrations of standard (dexamethasone) or compounds of the invention were incubated with transfected Hela cells for 72 hours. At the end of the incubation, substrate (p-nitrophenol acetate) for sPAP was added and the product measured by a spectrophotometric method. Increased absorbance reflected increased sPAP transcription and concentration-response lines were constructed such that EC$_{50}$-values could be estimated.

In this test, the isomers of Examples 1, 4, 5, 6, 7, 8, 12, 15, 16, 19, 22, 23 and 24 and the compound of Example 9 had EC$_{50}$-values of less than 400 nM.

Hydrolysis in Blood

All the isomer/compounds of the Examples were unstable in human plasma indicating that they are expected to possess an advantageous in vivo side effect profile. Compounds of examples 15, 16, 22 and 23 showed half-lives of less than 3 h whilst all isomers in the remaining examples showed half-lives of less than 60 min.

In Vivo (i) Anti-inflammatory Activity—Inhibition of rat ear oedema

The test compounds are dissolved in acetone and 40 ul containing 5% croton oil is applied to the inner surface of each of the ears of 60–80 g male rats. Animals are killed 6 hours later and the ears are removed. Standard size (0.5 cm diameter) discs are punched out and the discs weighed. Mean weight of the ear discs is calculated and from this percentage inhibition of ear inflammation in relation to croton oil alone treated ears are calculated.

| Compound | Dose | % Inhibition |
|---|---|---|
| Example 2 | 100 μg | 42 |
| Example 19 Isomer A | 100 μg | 54 |
| Example 19 Isomer B | 100 μg | 43 |
| Example 16 Isomer B | 10 μg | 42 |

(ii) Systemic effects—ACTH suppression in adrenalectomised rats

Male CD rats (90–120 g) were adrenalectomised under Isoflurane anaesthesia and drinking water was supplemented with 0.9% saline. Four days later the animals receive a single intra-tracheal dose (under Isoflurane anaesthesia) of compound suspended in saline (containing 0.2% Tween-80, 0.2 ml) at 10 am. After 4 h animals are sacrificed by administration of Euthetal and blood samples are taken by intra-cardiac puncture and collected into heparinised tubes. The samples are centrifuged (20 minutes at 1000 RPM at 4 deg C.), the plasma is collected and assayed by Radioimmunoassay (RIA) for Adrenocorticotrophic hormone (ACTH) using a DPC double antibody RIA kit. Intact and vehicle control groups were included in each experiment in order to account for diurnal variation in ACTH and effects of vehicle. Results are calculated with respect to the RIA standard curve and expressed as ACTH pg/ml plasma, allowing percentage reduction in ACTH to be calculated.

| Compound | Dose | % Reduction in ACTH |
|---|---|---|
| Fluocinolone acetonide | 1 μg | 49 |
| Fluocinolone acetonide | 5 μg | 84 |
| Example 2 | 500 μg | 0 |

This result illustrates the minimal systemic activity associated with these plasma labile derivatives.

Pharmaceutical Formulations

The following are examples of suitable formulations of compounds of the invention. The term "active ingredient" is used herein to represent a compound of the invention and can be, for example, the isomers (or a mixture thereof) of Examples 1, 12 or 19.

1. Inhalation Cartridges

| | |
|---|---|
| Active ingredient micronised | 1.6% w/w |
| Lactose BP | 98.4% w/w. |

The active ingredient is micronised in a conventional manner to a fine particle size range such as to permit inhalation of substantially all of the medicament into the lungs upon administration, prior to blending with normal tableting grade lactose in a high energy mixer. The powder blend is filled into gelatin capsules on a suitable encapsulating machine. The contents of the cartridges are administered using a powder inhaler such as ROTAHALER™ inhaler. Alternatively, the powder blend can be filled into blisters of a blister pack or strip. The contents of the blister pack or strip are administered using a powder inhaler such as DISKHALER™ or DISKUS™ inhaler. [ROTAHALER, DISKHALER and DISKUS are trade marks of the Glaxo Wellcome group of companies].

2. Aerosol Formulation (i) Suspension

|  | mg/actuation | per can |
|---|---|---|
| Active ingredient micronised | 0.25 | 40 mg |
| 1,1,1,2-tetrafluoroethane | 74.75 | 11.96 g |

The active ingredient is weighed directly into an open aluminium can and a metering valve is then crimped in place. 1,1,1,2-Tetrafluoroethane is then added to the can under pressure through the valve and the can shaken to disperse the drug. The resultant inhaler contains 0.33% w/w active ingredient.

(ii) Solution

|  | mg/actuation | per can |
|---|---|---|
| Active ingredient micronised | 0.25 | 40 mg |
| Ethanol (anhydrous) | 7.5 | 1.2 g |
| 1,1,1,2-tetrafluoroethane | 67.25 | 10.76 g |

Active ingredient is dissolved in the ethanol. The resultant ethanolic solution of active ingredient is metered into an open aluminium can and a metering valve is then crimped in place. 1,1,1,2-Tetrafluoroethane is then added under pressure through the valve. The resultant inhaler contains 0.33% w/w active ingredient and 10% w/w ethanol.

3. Cream

|  | % w/w |
|---|---|
| Active ingredient micronised | 0.2 |
| Liquid Paraffin | 40 |
| Cetostearyl alcohol | 5 |
| Cetomacrogol 1000 | 1 |
| Isopropylmyristate | 5 |
| Propylene glycol | 10 |
| Benzoic acid | 0.2 |
| Sodium phosphate | 0.05 |
| Citric acid/monohydrate | 0.05 |
| Purified water | to 100 |

The micronised active ingredient is dispersed in a portion of the water containing a portion of the cetomacrogol 1000. The liquid paraffin, cetostearyl alcohol and isopropyl myristate are melted together, cooled to 50 to 60° C. and added to the remaining water containing the propylene glycol, benzoic acid (preservative), and sodium phosphate and citric acid (buffering agents). The resultant oil phase is added to the active ingredient suspension with stirring until cool.

Protection may be sought for any subject matter described herein. Thus, protection may be sought for the compounds (including intermediates), compositions, processes and uses described herein.

What is claimed is:

1. A compound of formula (I)

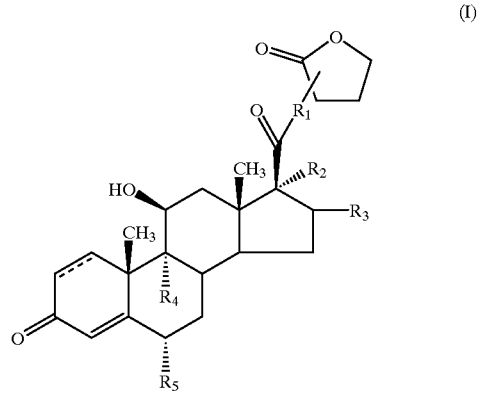

and solvates thereof, in which
$R_1$ represents O, S or NH;
$R_2$ individually represents $OC(=O)C_{1-6}$ alkyl;
$R_3$ individually represents hydrogen, methyl, which may be in either the α or β configuration or $=CH_2$;
or $R_2$ and $R_3$ together represent

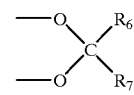

wherein $R_6$ and $R_7$ are the same or different and each represents hydrogen or $C_{1-6}$ alkyl;
$R_4$ and $R_5$ are the same or different and each represents hydrogen or halogen; and
═══ represents a single or a double bond.

2. A compound according to claim 1 in which $R_1$ represents O or S.

3. A compound according to claim 2 in which $R_1$ represents S.

4. A compound according to claim 1 in which $R_1$ is bonded to the alpha carbon atom of the lactone moiety.

5. A compound according to claim 1 in which $R_2$ individually represents $OC(=O)C_{1-6}$ alkyl.

6. A compound according to claim 5 in which $R_2$ represents $OC(=O)C_{1-3}$ alkyl.

7. A compound according to claim 5 in which $R_2$ represents $OC(=O)$ ethyl.

8. A compound according to claim 1 in which $R_3$ is methyl.

9. A compound according to claim 1 in which $R_2$ and $R_3$ together represent

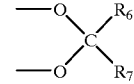

wherein $R_6$ and $R_7$ are the same or different and each represents hydrogen or $C_{1-6}$ alkyl.

10. A compound according to claim 9 in which $R_6$ and $R_7$ are the same or different and each represents hydrogen or $C_{1-3}$ alkyl.

11. A compound according to claim 9 in which $R_6$ and $R_7$ are the same or different and each represents hydrogen, methyl or n-propyl.

33

12. A compound according to claim 9 in which $R_6$ and $R_7$ are both methyl.

13. A compound according to claim 9 in which $R_6$ and $R_7$ are different and each represents hydrogen or n-propyl.

14. A compound according to claim 1 in which $R_4$ and $R_5$ are the same or different and each represents hydrogen, fluorine or chlorine.

15. A compound according to claim 1 in which $R_4$ and $R_5$ are the same or different and each represents hydrogen or fluorine.

16. A compound according to claim 1 in which both $R_4$ and $R_5$ are fluorine.

17. A compound according to claim 1 in which $R_1$ is S; $R_2$ is OC(=O)$C_{1-6}$ alkyl; $R_3$ is methyl; $R_4$ and $R_5$ are the same or different and each represents hydrogen or fluorine; and === represents a single or a double bond.

18. A compound according to claim 17 in which $R_2$ is OC(=O) ethyl and $R_4$ and $R_5$ are each fluorine.

19. A compound according to claim 1 in which $R_1$ is S; $R_2$ and $R_3$ together represent

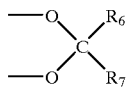

wherein $R_6$ and $R_7$ are the same or different and each represents hydrogen or $C_{1-6}$ alkyl; $R_4$ and $R_5$ which can be the same or different each represents hydrogen or fluorine, and === represents a single or a double bond.

20. A compound according to claim 19 in which $R_6$ and $R_7$ are the same or different and each represents hydrogen, methyl or n-propyl; and $R_4$ and $R_5$ are each fluorine.

21. 17α-Butyryloxy-6α,9α-difluoro-11β-hydroxy-16α-methyl-3-oxo-androsta-1,4-diene-17β-carbothioic acid S-(2-oxo-tetrahydro-furan-3-yl) ester;

17α-Acetyloxy-6α,9α-difluoro-11β-hydroxy-16α-methyl-3-oxo-androsta-1,4-diene-17β-carbothioic acid S-(2-oxo-tetrahydro-furan-3-yl) ester;

9α-Fluoro-11β-hydroxy-16β-methyl-3-oxo-17α-propionyloxy-androsta-1,4-diene-17β-carbothioic acid S-(2-oxo-tetrahydro-furan-3-yl) ester;

6α,9α-Difluoro-11β-hydroxy-16α-methyl-3-oxo-17α-propionyloxy-androsta-1,4-diene-17β-carbothioic acid S-(5-oxo-tetrahydro-furan-2-yl) ester;

6α,9α-Difluoro-11β-hydroxy-16α-methyl-3-oxo-17α-propionyloxy-androsta-1,4-diene-17β-carbothioic acid S-(2-oxo-tetrahydro-furan-4-yl) ester;

6α,9α-Difluoro-11β-hydroxy-16α-methyl-3-oxo-17α-propionyloxy-androsta-1,4-diene-17β-carboxylic acid (2-oxo-tetrahydro-furan-3-yl) ester;

6α,9α-Difluoro-11β-hydroxy-16α-methyl-3-oxo-17α-propionyloxy-androsta-1,4-diene-17β-carboxylic acid (2-oxo-tetrahydro-furan-5-yl) ester;

6α,9α-Difluoro-11β-hydroxy-16α,17α-isopropylidenedioxy-3-oxo-androsta-1,4-diene-17β-carbothioic acid S-(2-oxo-tetrahydro-furan-5-yl) ester;

6α,9α-Difluoro-11β-hydroxy-16α,17α-isopropylidenedioxy-3-oxo-androst-4-ene-17β-carbothioic acid S-(2-oxo-tetrahydro-furan-3-yl) ester;

6α,9α-Difluoro-11β-hydroxy-16α,17α-isopropylidenedioxy-3-oxo-androsta-1,4-diene-17β-carboxylic acid N-(2-oxo-tetrahydro-furan-3-yl) amide;

6α,9α-Difluoro-11β-hydroxy-16α,17α-isopropylidenedioxy-3-oxo-androsta-1,4-diene-17β-carboxylic acid (2-oxo-tetrahydro-furan-3-yl) ester;

34

16α,17α-Butylidenedioxy-11β-hydroxy-3-oxo-androsta-1,4-diene-17β-carbothioic acid S-(2-oxo-tetrahydro-furan-3-yl) ester;

16α,17α-(R-Butylidenedioxy)-6α,9α-difluoro-11β-hydroxy-3-oxo-androsta-1,4-diene-17β-carbothioic acid S-(2-oxo-tetrahydro-furan-3-yl) ester;

16α,17α-Butylidenedioxy-11β-hydroxy-3-oxo-androsta-1,4-diene-17β-carboxylic acid (2-oxo-tetrahydro-furan-3-yl) ester;

16α,17α-(R-Butylidenedioxy)-6α,9α-difluoro-11β-hydroxy-3-oxo-androst-4-ene-17β-carboxylic acid N-(2-oxo-tetrahydro-furan-3-yl) amide;

6α,9α-Difluoro-11β-hydroxy-16α,17α-isopropylidenedioxy-3-oxo-androsta-1,4-diene-17β-carboxylic acid N-(2-oxo-tetrahydro-furan-4-yl) amide;

6α,9α-Difluoro-11β-hydroxy-16-methyl-3-oxo-17α-propionyloxy-androst-4-ene-17β-carbothioic acid S-(2-oxo-tetrahydro-furan-3-yl) ester;

16α,17α-(R-Butylidenedioxy)-6α,9α-difluoro-11β-hydroxy-3-oxo-androst-4-ene-17β-carbothioic acid (5-oxo-tetrahydro-furan-2-yl) ester; and solvates thereof.

22. 6α,9α-Difluoro-11β-hydroxy-16α-methyl-3-oxo-17α-propionyloxy-androsta-1,4-diene-17β-carbothioic acid S-(2-oxo-tetrahydro-furan-3-yl) ester; and solvates thereof.

23. 6α,9α-Difluoro-11β-hydroxy-16α,17α-isopropylidenedioxy-3-oxo-androsta-1,4-diene-17β-carbothioic acid S-(2-oxo-tetrahydro-furan-3-yl) ester; and solvates thereof.

24. 16α,17α-(R-Butylidenedioxy)-6α,9α-difluoro-11β-hydroxy-3-oxo-androst-4-ene-17β-carbothioic acid S-(2-oxo-tetrahydro-furan-3-yl) ester; and solvates thereof.

25. A pharmaceutical composition comprising a compound of formula (I) as defined in claim 1 or a physiologically acceptable solvate thereof together, if desirable, in admixture with one or more physiologically acceptable diluents or carriers.

26. A method for the treatment of a human or animal subject with an anti-inflammatory and/or allergic condition, which method comprises administering to said human or animal subject an effective amount of a compound of formula (I) as defined in claim 1 or a physiologically acceptable solvate thereof.

27. A process for the preparation of a compound of formula (I) as defined in claim 1, which comprises A) treating a compound of formula (II)

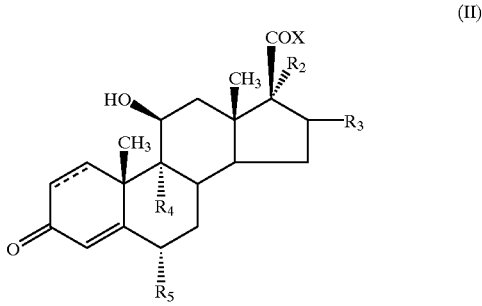

(II)

in which $R_2$, $R_3$, $R_4$, $R_5$ and === are as defined in claim 1 for compounds of formula (I) and X represents OH or an activated derivative thereof, with a compound of formula (III)

(III)

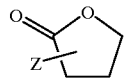

and salts thereof,
in which Z represents OH, NH$_2$ or SH;

B) for compounds of formula (I) wherein R$_1$ represents O or S, treating a compound of formula (II) in which R$_2$, R$_3$, R$_4$, R$_5$ and ═══ are as defined in claim 1 for compounds of formula (I) and X represents OH or SH or their corresponding salts, with a compound of formula (VI) or formula (VII)

(VI)

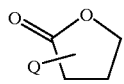

(VII)

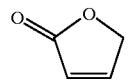

in which Q represents a suitable Cl, Br or OSO$_2$A group, wherein A is CH$_3$, CF$_3$ or p-CH$_3$C$_6$H$_4$;

C) conversion of a compound of formula (I) to a transacetylated, epimerized or esterified compound of formula (I); or D) deprotecting a hydroxyl protected derivative of a compound of formula (I), optionally followed by (i) solvate formation of (ii) preparation of an individual isomer of a compound of formula (I).

* * * * *